US007244590B2

(12) United States Patent
Lambeth et al.

(10) Patent No.: US 7,244,590 B2
(45) Date of Patent: Jul. 17, 2007

(54) REGULATORY PROTEIN FOR NOX ENZYMES

(75) Inventors: J. David Lambeth, Atlanta, GA (US); Guangjie Cheng, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 11/227,975

(22) Filed: Sep. 14, 2005

(65) Prior Publication Data

US 2006/0035358 A1 Feb. 16, 2006

Related U.S. Application Data

(62) Division of application No. 10/621,113, filed on Jul. 16, 2003, now Pat. No. 7,029,673.

(60) Provisional application No. 60/396,170, filed on Jul. 16, 2002, provisional application No. 60/405,647, filed on Aug. 23, 2002.

(51) Int. Cl.
*C12N 15/09* (2006.01)
*C12N 1/20* (2006.01)
*C12N 15/00* (2006.01)
*C07H 21/04* (2006.01)

(52) U.S. Cl. .................. 435/69.2; 435/189; 435/252.3; 435/320.1; 536/23.2

(58) Field of Classification Search ............... 435/69.2, 435/189, 252.3, 320.1; 536/23.2
See application file for complete search history.

(56) References Cited

U.S. PATENT DOCUMENTS 6,620,603 B1 9/2003 Lambeth et al.

FOREIGN PATENT DOCUMENTS

| WO | WO 00/28031 | 5/2000 |
| WO | WO 01/75067 | 10/2001 |
| WO | WO 01/87957 | 11/2001 |
| WO | WO 02/081703 | 10/2002 |

OTHER PUBLICATIONS

Burdon, "Superoxide and hydrogen peroxide in relation to mammalian cell proliferation," *Free Radical Biol. Med.*, 18(4):775-794 (1995).
Cheng, G. et al., *Gene*, 269:131:140 (May 16, 2001).
Cheng, Guangjie et al., *Journal of Biological Chemistry*, 279(6):4737-4742 (Feb. 6, 2004).
Cheng, Guangjie et al., *Journal of Biological Chemistry*, 279(33):34250-34255 (Aug. 13, 2004).
Church, S.L., et al., "Increased manganese superoxide dismutase expression suppresses the malignant phenotype of human melanoma cells," *Proc. Natl. Acad. Sci. USA* 90:3113-3117 (1993).
Dahan et al., "Mapping of Functional Domains in the p22$^{phox}$ Subunit of Flavocytochrome $b_{559}$ Participating in the Assembly of NADPH Oxidase Complex by Peptide Walking," *J. Biol. Chem.*, vol. 277, No. 10, pp. 8421-8432 (2002).
Edens, W., et al., "Tyrosine cross-linking of extracellular matrix is catalized by Duox, a multidomain oxidase/peroxidase with homology to the phagocyte oxidase subunit gp91*phox*, " *J. Cell Biol.* 154(4):879-91 (Aug. 20, 2001).
Fernandez-Pol, J.A., et al., "Correlation between the loss of the transformed phenotype and an increase in superoxide dismutase activity in a revertant subclone of sarcoma virus-infected mammalian cells," *Can. Res.* 42:609-617 (1982).
Fukui, T., et al., "p22phox mRNA expression and NADPH oxidase activity are increased in aortas from hypertensive rats," *Circ. Res.* 80(1):45-51 (1997).
Geiszt, Miklos et al., *Journal of Biological Chemistry*, 278(22):20006-20012 (May 30, 2003).
Griendling, K.K., et al., "Angiotensin II stimulates NADH and NADPH oxidase activity in cultured vascular smooth muscle cells." *Circ. Res.* 74(6):1141-1148 (1994).
Irani, K., et al., "Mitogenic signaling mediated by oxidants in ras-transfromed fibroblasts," *Science* 275(5306):1649-1652 (1997).
Lambeth, J.D., et al., "Novel homologs of gp91*phox*," *Trends Biochem. Sci.*, 10:459-461 (Oct. 25, 2000).
Li, Y., et al., "Validation of lucigenin (Bis-N-methylacridinium) as a chemilumigenic probe for detecting superoxide anion radical production by enzymatic cellular systems," *J. Biol. Chem.* 273(4):2015-2023 (1998).
Maly et al., "Restitution of Superoxide Generation in Autosomal Cytochrome-negative Chronic Granulomatous Disease (A22° CGD)-derived B Lymphocyte Cell Lines by Transfection with p22$^{phox}$ cDNA," *J. Exp. Med.*, 178:2047-2053 (1993).
Matsurbara, T., et al., "Increased superoxide anion release from human endothelial cells in response to cytokines," *J. Immun.* 137(10):3295-3298 (1986).
Meier, B., et al., "Human fibroblasts released reactive oxygen species in response to interleukin-1 or tumor necrosis factor-$\alpha$," *Biochem. j.* 263(2):539-545 (1989).
Pagano, P.J., et al., "Localization of a constitutively active, phagocyte-like NADPH oxidase in rabbit aortic adventitia: Enhancement by angiotensin II," *Proc. Natl. Acad. Sci. USA* 94(26):14483-14488 (1997).
Schmidt, K.N., et al., "The roles of hydrogen peroxide and superoxide as messengers in the activation of transcription factor NF-$\kappa$B," *Chem. & Biol.*, 2(1):13-22 (1995).
Schreck, R., et al., "Reactive oxygen intermediates as apparently widely used messengers in the activation of the NF-$\kappa$B transcription factor and HIV-1," *EMBO J.*, 10(8):2247-2258 (1991).

(Continued)

*Primary Examiner*—Tekchand Saidha
(74) *Attorney, Agent, or Firm*—Klarquist Sparkman LLP

(57) ABSTRACT

The present invention relates to nucleotides encoding for the production of novel regulatory proteins for Nox enzymes involved in generation of reactive oxygen intermediates that affect cell division. The present invention also provides vectors containing these nucleotides, cells transfected with these vectors, antibodies raised against these novel proteins, kits for detection, localization and measurement of these nucleotides and proteins, and methods to determine the activity of drugs to affect the biological activity of the regulatory proteins of the present invention.

20 Claims, 1 Drawing Sheet

OTHER PUBLICATIONS

Sumimoto et al., "Role of Src homology 3 domains in assembly and activation of the phagocyte NADPH oxidase," *Proc. Natl, Acad. Sci. USA*, vol. 91, pp. 5345-5349 (1994).

Sundaresan, M., et al., "Requirement for generation of $H_2O_2$ for platelet-derived growth factor signal transduction," *Science* 270:296-299 (1995).

Szatrowski, T.P., et al., "Production of large amounts of hydrogen peroxide by human tumor cells," *Canc. Res.* 51(3):794-798 (1991).

Takeya, Ryu et al., *Journal of Biological Chemistry*, 278(27):25234-25246 (Jul. 4, 2003).

Uhlinger, D.J., "Nucleoside triphosphate requirements for superoxide generation and phosphorylation in a cell-free system for hum neutrophils," 266(31):20990-20997 (1991).

Ushio-Fukai M., et al., "$p22^{phox}$ is a critical component of the superoxide-generating NADH/NADPH oxidase system and regulates angiotensin II-induced hypertrophy in vascular smooth muscle cells," *J. Biol. Chem.*, 271(38):23317-23321 (1996).

Yan, T., et al., Manganese-containing superoxide dismutase overexpression causes phenotypic reversion in SV40-transformed human lung fibroblasts, *Canc. Res.* 56:2864-2871 (1996).

Yu, L., et al., "Biosynthesis of the phagocyte NADPH oxidase cytochrome $b_{558}$," *J. Biol. Chem.*, 272(43):27288-27294 (1994).

Paulus et al., "NAD(P)H oxidase: a perpetrator of cardiovascular damage," www.servier.com/pro/cardiologie/pdfs/pau29ang.asp, Mar. 24, 2004.

Genbank Accession No. AAS89434, Apr. 22, 2004.

Genbank Accession No. AAG24891, Dec. 6, 2000.

SEQUENCE LISTING

<160> NUMBER OF SEQ ID NOS: 11

<210> SEQ ID NO 1
<211> LENGTH: 1129
<212> TYPE: DNA

<213> ORGANISM: Homo sapiens
<220> FEATURE:
<221> NAME/KEY: CDS
<222> LOCATION: (5)..(1114)
<223> OTHER INFORMATION:

<400> SEQUENCE: 1

```
agcc atg gca ggc ccc cga tac cca gtt tca gtg caa ggg gca gcc ctg      49
     Met Ala Gly Pro Arg Tyr Pro Val Ser Val Gln Gly Ala Ala Leu
     1               5                  10                  15 gtg cag atc aag agg ctc caa acg ttt gcc ttc tct gtg cgc tgg tca       97
Val Gln Ile Lys Arg Leu Gln Thr Phe Ala Phe Ser Val Arg Trp Ser
                 20                  25                  30 gac ggc agc gac acc ttc gtg cgc agg agt tgg gac gaa ttc agg cag      145
Asp Gly Ser Asp Thr Phe Val Arg Arg Ser Trp Asp Glu Phe Arg Gln
             35                  40                  45 ctc aag acc ctc aag gag acc ttc ccg gtg gag gcg ggc ctg ctg cgg      193
Leu Lys Thr Leu Lys Glu Thr Phe Pro Val Glu Ala Gly Leu Leu Arg
         50                  55                  60 aga tct gac cgc gtt ctc cca aag ctt ctc gat gca cca ctg ttg gga      241
Arg Ser Asp Arg Val Leu Pro Lys Leu Leu Asp Ala Pro Leu Leu Gly
 65                  70                  75 cgc gtg ggg cgc acg agc cgg ggc ctg gcg cgc ctg cag ctg ttg gaa      289
Arg Val Gly Arg Thr Ser Arg Gly Leu Ala Arg Leu Gln Leu Leu Glu
 80                  85                  90                  95 acc tat tct cgg agg ctg ctg gcg act gca gag cgc gtg gca cgg agc      337
Thr Tyr Ser Arg Arg Leu Leu Ala Thr Ala Glu Arg Val Ala Arg Ser
                100                 105                 110 ccg acg atc act ggc ttc ttc gca ccg caa ccc ctg gac ctg gag ccc      385
Pro Thr Ile Thr Gly Phe Phe Ala Pro Gln Pro Leu Asp Leu Glu Pro
            115                 120                 125 gcg ctg cca ccc ggc agc cgg gtg atc ctg ccc acc cca gag gag cag      433
Ala Leu Pro Pro Gly Ser Arg Val Ile Leu Pro Thr Pro Glu Glu Gln
        130                 135                 140 cct ctt tct cgc gct gcg ggc cgc ctc tcc atc cac agt ctg gag gct      481
Pro Leu Ser Arg Ala Ala Gly Arg Leu Ser Ile His Ser Leu Glu Ala
145                 150                 155 cag agc ctg cgc tgc ctg cag ccc ttc tgt acc cag gac acg cgg gat      529
Gln Ser Leu Arg Cys Leu Gln Pro Phe Cys Thr Gln Asp Thr Arg Asp
160                 165                 170                 175 agg cct ttt cag gcg cag gcc cag gag agc ctg gac gtg ctg ctg cgg      577
Arg Pro Phe Gln Ala Gln Ala Gln Glu Ser Leu Asp Val Leu Leu Arg
                180                 185                 190 cac ccc tca ggc tgg tgg ctg gtg gag aac gaa gac cgg cag acc gcc      625
His Pro Ser Gly Trp Trp Leu Val Glu Asn Glu Asp Arg Gln Thr Ala
            195                 200                 205 tgg ttt cca gcg ccc tac ctg gag gag gcg gcc ccg ggc caa ggc cgg      673
Trp Phe Pro Ala Pro Tyr Leu Glu Glu Ala Ala Pro Gly Gln Gly Arg
        210                 215                 220 gag gga ggc ccg tcc cta ggg agc agc ggt ccc cag ttc tgt gct tcc      721
Glu Gly Gly Pro Ser Leu Gly Ser Ser Gly Pro Gln Phe Cys Ala Ser
225                 230                 235 cgc gcc tac gag agc agc cgc gca gat gag ctg tcc gtg ccc gcg ggg      769
Arg Ala Tyr Glu Ser Ser Arg Ala Asp Glu Leu Ser Val Pro Ala Gly
240                 245                 250                 255 gcg cgc gtg cgc gtg ttg gaa acg tca gac cgc ggc tgg tgg cta tgc      817
Ala Arg Val Arg Val Leu Glu Thr Ser Asp Arg Gly Trp Trp Leu Cys
                260                 265                 270 agg tac ggc gac cgg gcg ggc cta ctc ccc gcg gtg ctg ctg cgg ccg      865
Arg Tyr Gly Asp Arg Ala Gly Leu Leu Pro Ala Val Leu Leu Arg Pro
            275                 280                 285
```

```
gaa ggg ctg ggc gct ctc ctg agc ggg acg ggg ttc cgt gga gga gac         913
Glu Gly Leu Gly Ala Leu Leu Ser Gly Thr Gly Phe Arg Gly Gly Asp
        290                 295                 300 gac ccg gcg ggt gag gcc cgg ggc ttc cct gaa ccc tcc cag gcc acc         961
Asp Pro Ala Gly Glu Ala Arg Gly Phe Pro Glu Pro Ser Gln Ala Thr
305                 310                 315 gcc cct ccc ccc acc gtg ccc acc cga cct tcg ccg ggc gcc atc cag        1009
Ala Pro Pro Pro Thr Val Pro Thr Arg Pro Ser Pro Gly Ala Ile Gln
320                 325                 330                 335 agc cgc tgc tgc acc gtc aca cgc agg gcc ctg gag cgg cgc cca cgg        1057
Ser Arg Cys Cys Thr Val Thr Arg Arg Ala Leu Glu Arg Arg Pro Arg
            340                 345                 350 cgc cag ggc cgc cct cga ggg tgc gtg gac tct gtg ccg cac ccc acg        1105
Arg Gln Gly Arg Pro Arg Gly Cys Val Asp Ser Val Pro His Pro Thr
        355                 360                 365 acg gag cag tgagcgcgag gatcc                                           1129
Thr Glu Gln
        370

<210> SEQ ID NO 2
<211> LENGTH: 370
<212> TYPE: PRT
<213> ORGANISM: Homo sapiens

<400> SEQUENCE: 2

Met Ala Gly Pro Arg Tyr Pro Val Ser Val Gln Gly Ala Ala Leu Val
1               5                   10                  15

Gln Ile Lys Arg Leu Gln Thr Phe Ala Phe Ser Val Arg Trp Ser Asp
            20                  25                  30

Gly Ser Asp Thr Phe Val Arg Arg Ser Trp Asp Glu Phe Arg Gln Leu
        35                  40                  45

Lys Thr Leu Lys Glu Thr Phe Pro Val Glu Ala Gly Leu Leu Arg Arg
    50                  55                  60

Ser Asp Arg Val Leu Pro Lys Leu Leu Asp Ala Pro Leu Leu Gly Arg
65                  70                  75                  80

Val Gly Arg Thr Ser Arg Gly Leu Ala Arg Leu Gln Leu Leu Glu Thr
                85                  90                  95

Tyr Ser Arg Arg Leu Leu Ala Thr Ala Glu Arg Val Ala Arg Ser Pro
            100                 105                 110

Thr Ile Thr Gly Phe Phe Ala Pro Gln Pro Leu Asp Leu Glu Pro Ala
        115                 120                 125

Leu Pro Pro Gly Ser Arg Val Ile Leu Pro Thr Pro Glu Glu Gln Pro
    130                 135                 140

Leu Ser Arg Ala Ala Gly Arg Leu Ser Ile His Ser Leu Glu Ala Gln
145                 150                 155                 160

Ser Leu Arg Cys Leu Gln Pro Phe Cys Thr Gln Asp Thr Arg Asp Arg
                165                 170                 175

Pro Phe Gln Ala Gln Ala Gln Glu Ser Leu Asp Val Leu Leu Arg His
            180                 185                 190

Pro Ser Gly Trp Trp Leu Val Glu Asn Glu Asp Arg Gln Thr Ala Trp
        195                 200                 205

Phe Pro Ala Pro Tyr Leu Glu Glu Ala Pro Gly Gln Gly Arg Glu
    210                 215                 220

Gly Gly Pro Ser Leu Gly Ser Ser Gly Pro Gln Phe Cys Ala Ser Arg
225                 230                 235                 240

Ala Tyr Glu Ser Ser Arg Ala Asp Glu Leu Ser Val Pro Ala Gly Ala
```

|  |  |  |  | 245 |  |  |  | 250 |  |  |  | 255 |  |  |
|---|---|---|---|---|---|---|---|---|---|---|---|---|---|---|
| Arg | Val | Arg | Val | Leu | Glu | Thr | Ser | Asp | Arg | Gly | Trp | Trp | Leu | Cys | Arg |
|  |  |  | 260 |  |  |  |  | 265 |  |  |  | 270 |  |  |  |

Tyr Gly Asp Arg Ala Gly Leu Leu Pro Ala Val Leu Leu Arg Pro Glu
            275                 280                 285

Gly Leu Gly Ala Leu Leu Ser Gly Thr Gly Phe Arg Gly Gly Asp Asp
            290                 295                 300

Pro Ala Gly Glu Ala Arg Gly Phe Pro Glu Pro Ser Gln Ala Thr Ala
305             310                 315                 320

Pro Pro Pro Thr Val Pro Thr Arg Pro Ser Pro Gly Ala Ile Gln Ser
                325                 330                 335

Arg Cys Cys Thr Val Thr Arg Arg Ala Leu Glu Arg Arg Pro Arg Arg
                340                 345                 350

Gln Gly Arg Pro Arg Gly Cys Val Asp Ser Val Pro His Pro Thr Thr
                355                 360                 365

Glu Gln
    370

<210> SEQ ID NO 3
<211> LENGTH: 1132
<212> TYPE: DNA
<213> ORGANISM: Homo sapiens
<220> FEATURE:
<221> NAME/KEY: CDS
<222> LOCATION: (5)..(1117)
<223> OTHER INFORMATION:

<400> SEQUENCE: 3

```
agcc atg gca ggc ccc cga tac cca gtt tca gtg caa ggg gca gcc ctg        49
     Met Ala Gly Pro Arg Tyr Pro Val Ser Val Gln Gly Ala Ala Leu
     1               5                   10                  15 gtg cag atc aag agg ctc caa acg ttt gcc ttc tct gtg cgc tgg tca        97
Val Gln Ile Lys Arg Leu Gln Thr Phe Ala Phe Ser Val Arg Trp Ser
                20                  25                  30 gac ggc agc gac acc ttc gtg cgc agg agt tgg gac gaa ttc agg cag       145
Asp Gly Ser Asp Thr Phe Val Arg Arg Ser Trp Asp Glu Phe Arg Gln
            35                  40                  45 ctc aag aag acc ctc aag gag acc ttc ccg gtg gag gcg ggc ctg ctg       193
Leu Lys Lys Thr Leu Lys Glu Thr Phe Pro Val Glu Ala Gly Leu Leu
        50                  55                  60 cgg aga tct gac cgc gtt ctc cca aag ctt ctc gat gca cca ctg ttg       241
Arg Arg Ser Asp Arg Val Leu Pro Lys Leu Leu Asp Ala Pro Leu Leu
    65                  70                  75 gga cgc gtg ggg cgc acg agc cgc ggc ctg gcg cgc ctg cag ctg ttg       289
Gly Arg Val Gly Arg Thr Ser Arg Gly Leu Ala Arg Leu Gln Leu Leu
80                  85                  90                  95 gaa acc tat tct cgg agg ctg ctg gcg act gca gag cgc gtg gca cgg       337
Glu Thr Tyr Ser Arg Arg Leu Leu Ala Thr Ala Glu Arg Val Ala Arg
                100                 105                 110 agc ccg acg atc act ggc ttc ttc gca ccg caa ccc ctg gac ctg gag       385
Ser Pro Thr Ile Thr Gly Phe Phe Ala Pro Gln Pro Leu Asp Leu Glu
            115                 120                 125 ccc gcg ctg cca ccc ggc agc cgg gtg atc ctg ccc acc cca gag gag       433
Pro Ala Leu Pro Pro Gly Ser Arg Val Ile Leu Pro Thr Pro Glu Glu
        130                 135                 140 cag cct ctt tct cgc gct gcg ggc cgc ctc tcc atc cac agt ctg gag       481
Gln Pro Leu Ser Arg Ala Ala Gly Arg Leu Ser Ile His Ser Leu Glu
    145                 150                 155 gct cag agc ctg cgc tgc ctg cag ccc ttc tgt acc cag gac acg cgg       529
```

-continued

```
Ala Gln Ser Leu Arg Cys Leu Gln Pro Phe Cys Thr Gln Asp Thr Arg
160             165                 170                 175 gat agg cct ttt cag gcg cag gcc cag gag agc ctg gac gtg ctg ctg      577
Asp Arg Pro Phe Gln Ala Gln Ala Gln Glu Ser Leu Asp Val Leu Leu
                180                 185                 190 cgg cac ccc tca ggc tgg tgg ctg gtg gag aac gaa gac cgg cag acc      625
Arg His Pro Ser Gly Trp Trp Leu Val Glu Asn Glu Asp Arg Gln Thr
            195                 200                 205 gcc tgg ttt cca gcg ccc tac ctg gag gag gcg gcc ccg ggc caa ggc      673
Ala Trp Phe Pro Ala Pro Tyr Leu Glu Glu Ala Ala Pro Gly Gln Gly
        210                 215                 220 cgg gag gga ggc ccg tcc cta ggg agc agc ggt ccc cag ttc tgt gct      721
Arg Glu Gly Gly Pro Ser Leu Gly Ser Ser Gly Pro Gln Phe Cys Ala
    225                 230                 235 tcc cgc gcc tac gag agc agc cgc gca gat gag ctg tcc gtg ccc gcg      769
Ser Arg Ala Tyr Glu Ser Ser Arg Ala Asp Glu Leu Ser Val Pro Ala
240                 245                 250                 255 ggg gcg cgc gtg cgc gtg ttg gaa acg tca gac cgc ggc tgg tgg cta      817
Gly Ala Arg Val Arg Val Leu Glu Thr Ser Asp Arg Gly Trp Trp Leu
                260                 265                 270 tgc agg tac ggc gac cgg gcg ggc cta ctc ccc gcg gtg ctg ctg cgg      865
Cys Arg Tyr Gly Asp Arg Ala Gly Leu Leu Pro Ala Val Leu Leu Arg
            275                 280                 285 ccg gaa ggg ctg ggc gct ctc ctg agc ggg acg ggg ttc cgt gga gga      913
Pro Glu Gly Leu Gly Ala Leu Leu Ser Gly Thr Gly Phe Arg Gly Gly
        290                 295                 300 gac gac ccg gcg ggt gag gcc cgg ggc ttc cct gaa ccc tcc cag gcc      961
Asp Asp Pro Ala Gly Glu Ala Arg Gly Phe Pro Glu Pro Ser Gln Ala
    305                 310                 315 acc gcc cct ccc ccc acc gtg ccc acc cga cct tcg ccg ggc gcc atc     1009
Thr Ala Pro Pro Pro Thr Val Pro Thr Arg Pro Ser Pro Gly Ala Ile
320                 325                 330                 335 cag agc cgc tgc tgc acc gtc aca cgc agg gcc ctg gag cgg cgc cca     1057
Gln Ser Arg Cys Cys Thr Val Thr Arg Arg Ala Leu Glu Arg Arg Pro
                340                 345                 350 cgg cgc cag ggc cgc cct cga ggg tgc gtg gac tct gtg ccg cac ccc     1105
Arg Arg Gln Gly Arg Pro Arg Gly Cys Val Asp Ser Val Pro His Pro
            355                 360                 365 acg acg gag cag tgagcgcgag gatcc                                    1132
Thr Thr Glu Gln
        370

<210> SEQ ID NO 4
<211> LENGTH: 371
<212> TYPE: PRT
<213> ORGANISM: Homo sapiens

<400> SEQUENCE: 4

Met Ala Gly Pro Arg Tyr Pro Val Ser Val Gln Gly Ala Ala Leu Val
1               5                   10                  15

Gln Ile Lys Arg Leu Gln Thr Phe Ala Phe Ser Val Arg Trp Ser Asp
                20                  25                  30

Gly Ser Asp Thr Phe Val Arg Ser Trp Asp Glu Phe Arg Gln Leu
            35                  40                  45

Lys Lys Thr Leu Lys Glu Thr Phe Pro Val Glu Ala Gly Leu Leu Arg
    50                  55                  60

Arg Ser Asp Arg Val Leu Pro Lys Leu Leu Asp Ala Pro Leu Leu Gly
65                  70                  75                  80

Arg Val Gly Arg Thr Ser Arg Gly Leu Ala Arg Leu Gln Leu Leu Glu
```

-continued

```
                    85                  90                  95
Thr Tyr Ser Arg Arg Leu Leu Ala Thr Ala Glu Arg Val Ala Arg Ser
                100                 105                 110

Pro Thr Ile Thr Gly Phe Phe Ala Pro Gln Pro Leu Asp Leu Glu Pro
            115                 120                 125

Ala Leu Pro Pro Gly Ser Arg Val Ile Leu Pro Thr Pro Glu Glu Gln
    130                 135                 140

Pro Leu Ser Arg Ala Ala Gly Arg Leu Ser Ile His Ser Leu Glu Ala
145                 150                 155                 160

Gln Ser Leu Arg Cys Leu Gln Pro Phe Cys Thr Gln Asp Thr Arg Asp
                165                 170                 175

Arg Pro Phe Gln Ala Gln Ala Gln Glu Ser Leu Asp Val Leu Leu Arg
            180                 185                 190

His Pro Ser Gly Trp Trp Leu Val Glu Asn Glu Asp Arg Gln Thr Ala
        195                 200                 205

Trp Phe Pro Ala Pro Tyr Leu Glu Glu Ala Ala Pro Gly Gln Gly Arg
    210                 215                 220

Glu Gly Gly Pro Ser Leu Gly Ser Ser Gly Pro Gln Phe Cys Ala Ser
225                 230                 235                 240

Arg Ala Tyr Glu Ser Ser Arg Ala Asp Glu Leu Ser Val Pro Ala Gly
                245                 250                 255

Ala Arg Val Arg Val Leu Glu Thr Ser Asp Arg Gly Trp Trp Leu Cys
            260                 265                 270

Arg Tyr Gly Asp Arg Ala Gly Leu Leu Pro Ala Val Leu Leu Arg Pro
        275                 280                 285

Glu Gly Leu Gly Ala Leu Leu Ser Gly Thr Gly Phe Arg Gly Gly Asp
    290                 295                 300

Asp Pro Ala Gly Glu Ala Arg Gly Phe Pro Glu Pro Ser Gln Ala Thr
305                 310                 315                 320

Ala Pro Pro Pro Thr Val Pro Thr Arg Pro Ser Pro Gly Ala Ile Gln
                325                 330                 335

Ser Arg Cys Cys Thr Val Thr Arg Arg Ala Leu Glu Arg Arg Pro Arg
            340                 345                 350

Arg Gln Gly Arg Pro Arg Gly Cys Val Asp Ser Val Pro His Pro Thr
        355                 360                 365

Thr Glu Gln
    370

<210> SEQ ID NO 5
<211> LENGTH: 1147
<212> TYPE: DNA
<213> ORGANISM: Homo sapiens
<220> FEATURE:
<221> NAME/KEY: CDS
<222> LOCATION: (5)..(1132)
<223> OTHER INFORMATION:

<400> SEQUENCE: 5 agcc atg gca ggc ccc cga tac cca gtt tca gtg caa ggg gca gcc ctg      49
     Met Ala Gly Pro Arg Tyr Pro Val Ser Val Gln Gly Ala Ala Leu
      1               5                  10                  15 gtg cag atc aag agg ctc caa acg ttt gcc ttc tct gtg cgc tgg tca       97
Val Gln Ile Lys Arg Leu Gln Thr Phe Ala Phe Ser Val Arg Trp Ser
                 20                  25                  30 gac ggc agc gac acc ttc gtg cgc agg agt tgg gac gaa ttc agg cag      145
Asp Gly Ser Asp Thr Phe Val Arg Arg Ser Trp Asp Glu Phe Arg Gln
             35                  40                  45
```

```
                                                          -continued ctc aag aag acc ctc aag gag acc ttc ccg gtg gag gcg ggc ctg ctg        193
Leu Lys Lys Thr Leu Lys Glu Thr Phe Pro Val Glu Ala Gly Leu Leu
        50                  55                  60 cgg aga tct gac cgc gtt ctc cca aag ctt ctc ggt cag gcc agc ctg        241
Arg Arg Ser Asp Arg Val Leu Pro Lys Leu Leu Gly Gln Ala Ser Leu
65                  70                  75 gat gca cca ctg ttg gga cgc gtg ggg cgc acg agc cgc ggc ctg gcg        289
Asp Ala Pro Leu Leu Gly Arg Val Gly Arg Thr Ser Arg Gly Leu Ala
80                  85                  90                  95 cgc ctg cag ctg ttg gaa acc tat tct cgg agg ctg ctg gcg act gca        337
Arg Leu Gln Leu Leu Glu Thr Tyr Ser Arg Arg Leu Leu Ala Thr Ala
                100                 105                 110 gag cgc gtg gca cgg agc ccg acg atc act ggc ttc ttc gca ccg caa        385
Glu Arg Val Ala Arg Ser Pro Thr Ile Thr Gly Phe Phe Ala Pro Gln
            115                 120                 125 ccc ctg gac ctg gag ccc gcg ctg cca ccc ggc agc cgg gtg atc ctg        433
Pro Leu Asp Leu Glu Pro Ala Leu Pro Pro Gly Ser Arg Val Ile Leu
        130                 135                 140 ccc acc cca gag gag cag cct ctt tct cgc gct gcg ggc cgc ctc tcc        481
Pro Thr Pro Glu Glu Gln Pro Leu Ser Arg Ala Ala Gly Arg Leu Ser
145                 150                 155 atc cac agt ctg gag gct cag agc ctg cgc tgc ctg cag ccc ttc tgt        529
Ile His Ser Leu Glu Ala Gln Ser Leu Arg Cys Leu Gln Pro Phe Cys
160                 165                 170                 175 acc cag gac acg cgg gat agg cct ttt cag gcg cag gcc cag gag agc        577
Thr Gln Asp Thr Arg Asp Arg Pro Phe Gln Ala Gln Ala Gln Glu Ser
                180                 185                 190 ctg gac gtg ctg ctg cgg cac ccc tca ggc tgg tgg ctg gtg gag aac        625
Leu Asp Val Leu Leu Arg His Pro Ser Gly Trp Trp Leu Val Glu Asn
            195                 200                 205 gaa gac cgg cag acc gcc tgg ttt cca gcg ccc tac ctg gag gag gcg        673
Glu Asp Arg Gln Thr Ala Trp Phe Pro Ala Pro Tyr Leu Glu Glu Ala
        210                 215                 220 gcc ccg ggc caa ggc cgg gag gga ggc ccg tcc cta ggg agc agc ggt        721
Ala Pro Gly Gln Gly Arg Glu Gly Gly Pro Ser Leu Gly Ser Ser Gly
225                 230                 235 ccc cag ttc tgt gct tcc cgc gcc tac gag agc agc cgc gca gat gag        769
Pro Gln Phe Cys Ala Ser Arg Ala Tyr Glu Ser Ser Arg Ala Asp Glu
240                 245                 250                 255 ctg tcc gtg ccc gcg ggg gcg cgc gtg cgc gtg ttg gaa acg tca gac        817
Leu Ser Val Pro Ala Gly Ala Arg Val Arg Val Leu Glu Thr Ser Asp
                260                 265                 270 cgc ggc tgg tgg cta tgc agg tac ggc gac cgg gcg ggc cta ctc ccc        865
Arg Gly Trp Trp Leu Cys Arg Tyr Gly Asp Arg Ala Gly Leu Leu Pro
            275                 280                 285 gcg gtg ctg ctg cgg ccg gaa ggg ctg ggc gct ctc ctg agc ggg acg        913
Ala Val Leu Leu Arg Pro Glu Gly Leu Gly Ala Leu Leu Ser Gly Thr
        290                 295                 300 ggg ttc cgt gga gga gac gac ccg gcg ggt gag gcc cgg ggc ttc cct        961
Gly Phe Arg Gly Gly Asp Asp Pro Ala Gly Glu Ala Arg Gly Phe Pro
305                 310                 315 gaa ccc tcc cag gcc acc gcc cct ccc ccc acc gtg ccc acc cga cct       1009
Glu Pro Ser Gln Ala Thr Ala Pro Pro Pro Thr Val Pro Thr Arg Pro
320                 325                 330                 335 tcg ccg ggc gcc atc cag agc cgc tgc tgc acc gtc aca cgc agg gcc       1057
Ser Pro Gly Ala Ile Gln Ser Arg Cys Cys Thr Val Thr Arg Arg Ala
                340                 345                 350 ctg gag cgg cgc cca cgg cgc cag ggc cgc cct cga ggg tgc gtg gac       1105
Leu Glu Arg Arg Pro Arg Arg Gln Gly Arg Pro Arg Gly Cys Val Asp
```

```
            355                 360                 365
tct gtg ccg cac ccc acg acg gag cag tgagcgcgag gatcc            1147
Ser Val Pro His Pro Thr Thr Glu Gln
        370                 375

<210> SEQ ID NO 6
<211> LENGTH: 376
<212> TYPE: PRT
<213> ORGANISM: Homo sapiens

<400> SEQUENCE: 6

Met Ala Gly Pro Arg Tyr Pro Val Ser Val Gln Gly Ala Ala Leu Val
1               5                   10                  15

Gln Ile Lys Arg Leu Gln Thr Phe Ala Phe Ser Val Arg Trp Ser Asp
            20                  25                  30

Gly Ser Asp Thr Phe Val Arg Arg Ser Trp Asp Glu Phe Arg Gln Leu
        35                  40                  45

Lys Lys Thr Leu Lys Glu Thr Phe Pro Val Glu Ala Gly Leu Leu Arg
    50                  55                  60

Arg Ser Asp Arg Val Leu Pro Lys Leu Leu Gly Gln Ala Ser Leu Asp
65                  70                  75                  80

Ala Pro Leu Leu Gly Arg Val Gly Arg Thr Ser Arg Gly Leu Ala Arg
                85                  90                  95

Leu Gln Leu Leu Glu Thr Tyr Ser Arg Arg Leu Leu Ala Thr Ala Glu
            100                 105                 110

Arg Val Ala Arg Ser Pro Thr Ile Thr Gly Phe Phe Ala Pro Gln Pro
        115                 120                 125

Leu Asp Leu Glu Pro Ala Leu Pro Pro Gly Ser Arg Val Ile Leu Pro
    130                 135                 140

Thr Pro Glu Glu Gln Pro Leu Ser Arg Ala Ala Gly Arg Leu Ser Ile
145                 150                 155                 160

His Ser Leu Glu Ala Gln Ser Leu Arg Cys Leu Gln Pro Phe Cys Thr
                165                 170                 175

Gln Asp Thr Arg Asp Arg Pro Phe Gln Ala Gln Ala Gln Glu Ser Leu
            180                 185                 190

Asp Val Leu Leu Arg His Pro Ser Gly Trp Trp Leu Val Glu Asn Glu
        195                 200                 205

Asp Arg Gln Thr Ala Trp Phe Pro Ala Pro Tyr Leu Glu Glu Ala Ala
    210                 215                 220

Pro Gly Gln Gly Arg Glu Gly Gly Pro Ser Leu Gly Ser Ser Gly Pro
225                 230                 235                 240

Gln Phe Cys Ala Ser Arg Ala Tyr Glu Ser Ser Arg Ala Asp Glu Leu
                245                 250                 255

Ser Val Pro Ala Gly Ala Arg Val Arg Val Leu Glu Thr Ser Asp Arg
            260                 265                 270

Gly Trp Trp Leu Cys Arg Tyr Gly Asp Arg Ala Gly Leu Leu Pro Ala
        275                 280                 285

Val Leu Leu Arg Pro Glu Gly Leu Gly Ala Leu Leu Ser Gly Thr Gly
    290                 295                 300

Phe Arg Gly Gly Asp Asp Pro Ala Gly Glu Ala Arg Gly Phe Pro Glu
305                 310                 315                 320

Pro Ser Gln Ala Thr Ala Pro Pro Thr Val Pro Thr Arg Pro Ser
                325                 330                 335

Pro Gly Ala Ile Gln Ser Arg Cys Cys Thr Val Thr Arg Arg Ala Leu
            340                 345                 350
```

Glu Arg Arg Pro Arg Arg Gln Gly Arg Pro Arg Gly Cys Val Asp Ser
                355                 360                 365

Val Pro His Pro Thr Thr Glu Gln
    370                 375

<210> SEQ ID NO 7
<211> LENGTH: 1144
<212> TYPE: DNA
<213> ORGANISM: Homo sapiens
<220> FEATURE:
<221> NAME/KEY: CDS
<222> LOCATION: (5)..(1129)
<223> OTHER INFORMATION:

<400> SEQUENCE: 7

| | | |
|---|---|---|
| agcc atg gca ggc ccc cga tac cca gtt tca gtg caa ggg gca gcc ctg | 49 |
|      Met Ala Gly Pro Arg Tyr Pro Val Ser Val Gln Gly Ala Ala Leu | |
|        1               5                  10                 15  | |
| gtg cag atc aag agg ctc caa acg ttt gcc ttc tct gtg cgc tgg tca | 97 |
| Val Gln Ile Lys Arg Leu Gln Thr Phe Ala Phe Ser Val Arg Trp Ser | |
|              20                  25                  30         | |
| gac ggc agc gac acc ttc gtg cgc agg agt tgg gac gaa ttc agg cag | 145 |
| Asp Gly Ser Asp Thr Phe Val Arg Arg Ser Trp Asp Glu Phe Arg Gln | |
|         35                  40                  45              | |
| ctc aag acc ctc aag gag acc ttc ccg gtg gag gcg ggc ctg ctg cgg | 193 |
| Leu Lys Thr Leu Lys Glu Thr Phe Pro Val Glu Ala Gly Leu Leu Arg | |
|     50                  55                  60                  | |
| aga tct gac cgc gtt ctc cca aag ctt ctc ggt cag gcc agc ctg gat | 241 |
| Arg Ser Asp Arg Val Leu Pro Lys Leu Leu Gly Gln Ala Ser Leu Asp | |
| 65                  70                  75                      | |
| gca cca ctg ttg gga cgc gtg ggg cgc acg agc cgc ggc ctg gcg cgc | 289 |
| Ala Pro Leu Leu Gly Arg Val Gly Arg Thr Ser Arg Gly Leu Ala Arg | |
| 80                  85                  90                  95  | |
| ctg cag ctg ttg gaa acc tat tct cgg agg ctg ctg gcg act gca gag | 337 |
| Leu Gln Leu Leu Glu Thr Tyr Ser Arg Arg Leu Leu Ala Thr Ala Glu | |
|                 100                 105                 110     | |
| cgc gtg gca cgg agc ccg acg atc act ggc ttc ttc gca ccg caa ccc | 385 |
| Arg Val Ala Arg Ser Pro Thr Ile Thr Gly Phe Phe Ala Pro Gln Pro | |
|             115                 120                 125         | |
| ctg gac ctg gag ccc gcg ctg cca ccc ggc agc cgg gtg atc ctg ccc | 433 |
| Leu Asp Leu Glu Pro Ala Leu Pro Pro Gly Ser Arg Val Ile Leu Pro | |
|         130                 135                 140             | |
| acc cca gag gag cag cct ctt tct cgc gct gcg ggc cgc ctc tcc atc | 481 |
| Thr Pro Glu Glu Gln Pro Leu Ser Arg Ala Ala Gly Arg Leu Ser Ile | |
|     145                 150                 155                 | |
| cac agt ctg gag gct cag agc ctg cgc tgc ctg cag ccc ttc tgt acc | 529 |
| His Ser Leu Glu Ala Gln Ser Leu Arg Cys Leu Gln Pro Phe Cys Thr | |
| 160                 165                 170                 175 | |
| cag gac acg cgg gat agg cct ttt cag gcg cag gcc cag gag agc ctg | 577 |
| Gln Asp Thr Arg Asp Arg Pro Phe Gln Ala Gln Ala Gln Glu Ser Leu | |
|                 180                 185                 190     | |
| gac gtg ctg ctg cgg cac ccc tca ggc tgg tgg ctg gtg gag aac gaa | 625 |
| Asp Val Leu Leu Arg His Pro Ser Gly Trp Trp Leu Val Glu Asn Glu | |
|             195                 200                 205         | |
| gac cgg cag acc gcc tgg ttt cca gcg ccc tac ctg gag gag gcg gcc | 673 |
| Asp Arg Gln Thr Ala Trp Phe Pro Ala Pro Tyr Leu Glu Glu Ala Ala | |
|         210                 215                 220             | |
| ccg ggc caa ggc cgg gag gga ggc ccg tcc cta ggg agc agc ggt ccc | 721 |
| Pro Gly Gln Gly Arg Glu Gly Gly Pro Ser Leu Gly Ser Ser Gly Pro | |
|     225                 230                 235                 | |

-continued

| | | |
|---|---|---|
| cag ttc tgt gct tcc cgc gcc tac gag agc agc cgc gca gat gag ctg<br>Gln Phe Cys Ala Ser Arg Ala Tyr Glu Ser Ser Arg Ala Asp Glu Leu<br>240                        245                    250                    255 | 769 |
| tcc gtg ccc gcg ggg gcg cgc gtg cgc gtg ttg gaa acg tca gac cgc<br>Ser Val Pro Ala Gly Ala Arg Val Arg Val Leu Glu Thr Ser Asp Arg<br>                    260                    265                    270 | 817 |
| ggc tgg tgg cta tgc agg tac ggc gac cgg gcg ggc cta ctc ccc gcg<br>Gly Trp Trp Leu Cys Arg Tyr Gly Asp Arg Ala Gly Leu Leu Pro Ala<br>                  275                    280                    285 | 865 |
| gtg ctg ctg cgg ccg gaa ggg ctg ggc gct ctc ctg agc ggg acg ggg<br>Val Leu Leu Arg Pro Glu Gly Leu Gly Ala Leu Leu Ser Gly Thr Gly<br>            290                    295                    300 | 913 |
| ttc cgt gga gga gac gac ccg gcg ggt gag gcc cgg ggc ttc cct gaa<br>Phe Arg Gly Gly Asp Asp Pro Ala Gly Glu Ala Arg Gly Phe Pro Glu<br>305                        310                    315 | 961 |
| ccc tcc cag gcc acc gcc cct ccc acc gtg ccc acc cga cct tcg<br>Pro Ser Gln Ala Thr Ala Pro Pro Thr Val Pro Thr Arg Pro Ser<br>320                        325                    330                    335 | 1009 |
| ccg ggc gcc atc cag agc cgc tgc tgc acc gtc aca cgc agg gcc ctg<br>Pro Gly Ala Ile Gln Ser Arg Cys Cys Thr Val Thr Arg Arg Ala Leu<br>                    340                    345                    350 | 1057 |
| gag cgg cgc cca cgg cgc cag ggc cgc cct cga ggg tgc gtg gac tct<br>Glu Arg Arg Pro Arg Arg Gln Gly Arg Pro Arg Gly Cys Val Asp Ser<br>            355                    360                    365 | 1105 |
| gtg ccg cac ccc acg acg gag cag tgagcgcgag gatcc<br>Val Pro His Pro Thr Thr Glu Gln<br>          370                    375 | 1144 |

<210> SEQ ID NO 8
<211> LENGTH: 375
<212> TYPE: PRT
<213> ORGANISM: Homo sapiens

<400> SEQUENCE: 8

Met Ala Gly Pro Arg Tyr Pro Val Ser Val Gln Gly Ala Ala Leu Val
1               5                   10                  15

Gln Ile Lys Arg Leu Gln Thr Phe Ala Phe Ser Val Arg Trp Ser Asp
                20                  25                  30

Gly Ser Asp Thr Phe Val Arg Arg Ser Trp Asp Glu Phe Arg Gln Leu
            35                  40                  45

Lys Thr Leu Lys Glu Thr Phe Pro Val Glu Ala Gly Leu Leu Arg Arg
        50                  55                  60

Ser Asp Arg Val Leu Pro Lys Leu Leu Gly Gln Ala Ser Leu Asp Ala
65                  70                  75                  80

Pro Leu Leu Gly Arg Val Gly Arg Thr Ser Arg Gly Leu Ala Arg Leu
                85                  90                  95

Gln Leu Leu Glu Thr Tyr Ser Arg Arg Leu Leu Ala Thr Ala Glu Arg
            100                 105                 110

Val Ala Arg Ser Pro Thr Ile Thr Gly Phe Phe Ala Pro Gln Pro Leu
        115                 120                 125

Asp Leu Glu Pro Ala Leu Pro Pro Gly Ser Arg Val Ile Leu Pro Thr
130                 135                 140

Pro Glu Glu Gln Pro Leu Ser Arg Ala Ala Gly Arg Leu Ser Ile His
145                 150                 155                 160

Ser Leu Glu Ala Gln Ser Leu Arg Cys Leu Gln Pro Phe Cys Thr Gln
                165                 170                 175

Asp Thr Arg Asp Arg Pro Phe Gln Ala Gln Ala Gln Glu Ser Leu Asp
            180                 185                 190

Val Leu Leu Arg His Pro Ser Gly Trp Trp Leu Val Glu Asn Glu Asp
            195                 200                 205

Arg Gln Thr Ala Trp Phe Pro Ala Pro Tyr Leu Glu Glu Ala Ala Pro
    210                 215                 220

Gly Gln Gly Arg Glu Gly Gly Pro Ser Leu Gly Ser Ser Gly Pro Gln
225                 230                 235                 240

Phe Cys Ala Ser Arg Ala Tyr Glu Ser Ser Arg Ala Asp Glu Leu Ser
                245                 250                 255

Val Pro Ala Gly Ala Arg Val Arg Val Leu Glu Thr Ser Asp Arg Gly
            260                 265                 270

Trp Trp Leu Cys Arg Tyr Gly Asp Arg Ala Gly Leu Leu Pro Ala Val
            275                 280                 285

Leu Leu Arg Pro Glu Gly Leu Gly Ala Leu Leu Ser Gly Thr Gly Phe
    290                 295                 300

Arg Gly Gly Asp Asp Pro Ala Gly Glu Ala Arg Gly Phe Pro Glu Pro
305                 310                 315                 320

Ser Gln Ala Thr Ala Pro Pro Thr Val Pro Thr Arg Pro Ser Pro
                325                 330                 335

Gly Ala Ile Gln Ser Arg Cys Cys Thr Val Thr Arg Arg Ala Leu Glu
            340                 345                 350

Arg Arg Pro Arg Arg Gln Gly Arg Pro Arg Gly Cys Val Asp Ser Val
    355                 360                 365

Pro His Pro Thr Thr Glu Gln
    370                 375

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
aaacgtcaga ccgcggctgg tggc                                           24

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
gtccatcccc tcatcgggat cctc                                           24

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
tcaggaatct gcagcctgga agcc                                           24

REGULATORY PROTEIN FOR NOX ENZYMES

CROSS REFERENCE TO RELATED APPLICATIONS

This application claims priority to U.S. application Ser. No. 10/621,113, filed Jul. 16, 2003, which issued as U.S. Pat. No. 7,029,673. and which is incorporated by reference herein in its entirety. U.S. application Ser. No. 10/621,113 claims the benefit of U.S. Provisional Patent Application No. 60/396,170, filed Jul. 16, 2002 and U.S. Provisional Patent Application No. 60/405,647, filed Aug. 23, 2002.

The U.S. Government has a paid-up license in this invention and the right in limited circumstances to require the patent owner to license others on reasonable terms as provided for by the terms of National Institutes of Health grant CA84138.

TECHNICAL FIELD

The present invention relates to the field of normal and abnormal cell growth, in particular mitogenic regulation. The present invention provides the following: nucleotide sequences encoding for regulatory proteins for enzymes that are mitogenic regulators; amino acid sequences of these regulatory proteins; vectors containing these nucleotide sequences; methods for transfecting cells with vectors that produce these regulatory proteins; transfected cells; methods for administering these transfected cells to animals to induce tumor formation; antibodies to these proteins that are useful for detecting and measuring levels of these proteins, and for binding to cells possessing extracellular epitopes of these proteins; and assays for screening for effectors of these proteins.

BACKGROUND OF THE INVENTION

Reactive oxygen intermediates (ROI) are cytotoxic and mutagenic. They modify and damage critical biomolecules including DNA and lipids. The partial reduction products of oxygen are: 1 electron reduces $O_2$ to form superoxide ($O_2^-$), and 2 electrons reduce $O_2$ to form hydrogen peroxide ($H_2O_2$). The cytotoxic property of ROI is exploited by phagocytes, which generate large amounts of superoxide and hydrogen peroxide as part of their armory of bactericidal mechanisms. ROI have been considered an accidental byproduct of metabolism, particularly mitochondrial respiration. However, recent studies give evidence for regulated enzymatic generation of $O_2^-$ and its conversion to $H_2O_2$ in a variety of cells. The conversion of $O_2^-$ to $H_2O_2$ can also occur spontaneously, but is markedly accelerated by superoxide dismutase (SOD). Exposure of cells to platelet derived growth factor and epidermal growth factor induces the production of $H_2O_2$, which activates components of signaling pathways including p42/p44 MAPK and tyrosine phosphorylation.

Several biological systems generate reactive oxygen. Exposure of neutrophils to bacteria or to various soluble mediators such as formyl-Met-Leu-Phe or phorbol esters activates a massive consumption of oxygen, termed the respiratory burst, to initially generate superoxide, with secondary generation of $H_2O_2$, HOCl and hydroxyl radicals. The enzyme responsible for this oxygen consumption is the respiratory burst oxidase (nicotinamide adenine dinucleotide phosphate-reduced form (NADPH) oxidase).

There is growing evidence for the generation of ROI by non-phagocytic cells, particularly in situations related to cell proliferation. Significant generation of $H_2O_2$, $O_2^-$, or both have been noted in some cell types. Fibroblasts and human endothelial cells show increased release of superoxide in response to cytokines such as interleukin-1 or tumor necrosis factor (TNF) (Meier et al. (1989) *Biochem J.* 263, 539-545; Matsubara et al. (1986) *J. Immun.* 137, 3295-3298). Ras-transformed fibroblasts show increased superoxide release compared with control fibroblasts (Irani, et al. (1997) *Science* 275, 1649-1652). Rat vascular smooth muscle cells show increased $H_2O_2$ release in response to PDGF (Sundaresan et al. (1995) *Science* 270, 296-299) and angiotensin II (Griendling et al. (1994) *Circ. Res.* 74, 1141-1148; Fukui et al. (1997) *Circ. Res.* 80, 45-51; Ushio-Fukai et al. (1996) *J. Biol. Chem.* 271, 23317-23321), and $H_2O_2$ in these cells is associated with increased proliferation rate. $H_2O_2$ in the transformed fibroblasts and in vascular smooth muscle cells is associated with an increased proliferation rate. The occurrence of ROI in a variety of cell types is summarized in Table 1 (adapted from Burdon, R. (1995) *Free Radical Biol. Med.* 18, 775-794).

TABLE 1

| Superoxide | Hydrogen Peroxide |
|---|---|
| human fibroblasts | Balb/3T3 cells |
| human endothelial cells | rat pancreatic islet cells |
| human/rat smooth muscle cells | murine keratinocytes |
| human fat cells | rabbit chondrocytes |
| human osteocytes | human tumor cells |
| BHK-21 cells | fat cells, 3T3 L1 cells |
| human colonic epithelial cells | |

ROI generated by neutrophils have a cytotoxic function. While ROI are normally directed at the invading microbe, ROI can also induce tissue damage (e.g., in inflammatory conditions such as arthritis, shock, lung disease, and inflammatory bowel disease) or may be involved in tumor initiation or promotion, due to damaging effects on DNA. Nathan (Szatrowski et al. (1991) *Canc. Res.* 51, 794-798) proposed that the generation of ROI in tumor cells may contribute to the hypermutability seen in tumors, and may therefore contribute to tumor heterogeneity, invasion and metastasis.

In addition to cytotoxic and mutagenic roles, ROI have ideal properties as signal molecules: 1) they are generated in a controlled manner in response to upstream signals; 2) the signal can be terminated by rapid metabolism of $O_2^-$ and $H_2O_2$ by SOD and catalase/peroxidases; 3) they elicit downstream effects on target molecules, e.g., redox-sensitive regulatory proteins such as NFκ-B and AP-1 (Schreck et al. (1991) *EMBO J.* 10, 2247-2258; Schmidt et al. (1995) *Chemistry & Biology* 2, 13-22). Oxidants such as $O_2^-$ and $H_2O_2$ have a relatively well defined signaling role in bacteria, operating via the SoxI/II regulon to regulate transcription.

ROI appear to have a direct role in regulating cell division, and may function as mitogenic signals in pathological conditions related to growth. These conditions include cancer and cardiovascular disease. $O_2^-$ is generated in endothelial cells in response to cytokines, and might play a role in angiogenesis (Matsubara et al. (1986) *J. Immun.* 137, 3295-3298). $O_2^-$ and $H_2O_2$ are also proposed to function as "life-signals", preventing cells from undergoing apoptosis (Matsubara et al. (1986) *J. Immun.* 137, 3295-3298). As discussed above, many cells respond to growth factors (e.g., platelet derived growth factor (PDGF), epidermal derived growth factor (EGF), angiotensin II, and various cytokines) with both increased production of $O_2^-/H_2O_2$ and increased proliferation. Inhibition of ROI generation prevents the mitogenic response. Exposure to exogenously generated $O_2^-$ and $H_2O_2$ results in an increase in cell proliferation. A partial list of responsive cell types is shown below in Table 2 (adapted from Burdon, R. (1995) *Free Radical Biol. Med.* 18, 775-794).

TABLE 2

| Superoxide | Hydrogen peroxide |
| --- | --- |
| human, hamster fibroblasts | mouse osteoblastic cells |
| Balb/3T3 cells | Balb/3T3 cells |
| human histiocytic leukemia | rat, hamster fibroblasts |
| mouse epidermal cells | human smooth muscle cells |
| rat colonic epithelial cells | rat vascular smooth muscle cells |
| rat vascular smooth muscle cells | |

While non-transformed cells can respond to growth factors and cytokines with the production of ROI, tumor cells appear to produce ROI in an uncontrolled manner. A series of human tumor cells produced large amounts of hydrogen peroxide compared with non-tumor cells (Szatrowski et al. (1991) *Canc. Res.* 51, 794-798). Ras-transformed NIH 3T3 cells generated elevated amounts of superoxide, and inhibition of superoxide generation by several mechanisms resulted in a reversion to a "normal" growth phenotype.

$O_2^-$ has been implicated in maintenance of the transformed phenotype in cancer cells including melanoma, breast carcinoma, fibrosarcoma, and virally transformed tumor cells. Decreased levels of the manganese form of SOD (MnSOD) have been measured in cancer cells and in vitro-transformed cell lines, predicting increased $O_2^-$ levels (Burdon, R. (1995) *Free Radical Biol. Med.* 18, 775-794). MnSOD is encoded on chromosome 6q25 which is very often lost in melanoma. Overexpression of MnSOD in melanoma and other cancer cells (Church et al. (1993) *Proc. of Natl. Acad. Sci.* 90, 3113-3117; Fernandez-Pol et al. (1982) *Canc. Res.* 42, 609-617; Yan et al. (1996) *Canc. Res.* 56, 2864-2871) resulted in suppression of the transformed phenotype.

ROI are implicated in the growth of vascular smooth muscle associated with hypertension, atherosclerosis, and restenosis after angioplasty. $O_2^-$ generation is seen in rabbit aortic adventitia (Pagano et al. (1997) *Proc. Natl. Acad. Sci.* 94, 14483-14488). Vascular endothelial cells release $O_2^-$ in response to cytokines (Matsubara et al. (1986) *J Immun.* 137, 3295-3298). $O_2^-$ is also generated by aortic smooth muscle cells in culture, and increased $O_2^-$-generation is stimulated by angiotensin II which also induces cell hypertrophy. In a rat model system, infusion of angiotensin II leads to hypertension as well as increased $O_2^-$ generation in subsequently isolated aortic tissue (Ushio-Fukai et al. (1996) *J. Biol. Chem.* 271, 23317-23321; Yu et al. (1997) *J. Biol. Chem.* 272, 27288-27294). Intravenous infusion of a form of SOD that localizes to the vasculature or an infusion of an $O_2^-$ scavenger prevented angiotensin II induced hypertension and inhibited ROI generation (Fukui et al. (1997) *Circ. Res.* 80, 45-51).

The neutrophil NADPH oxidase, also known as phagocyte respiratory burst oxidase, provides a paradigm for the study of the specialized enzymatic ROI-generating system. This extensively studied enzyme oxidizes NADPH and reduces oxygen to form $O_2^-$. NADPH oxidase consists of multiple proteins and is regulated by assembly of cytosolic and membrane components. The catalytic moiety consists of flavocytochrome $b_{558}$, an integral plasma membrane enzyme comprised of two components: gp91phox (gp refers to glycoprotein; phox is an abbreviation of the words phagocyte and oxidase) and p22phox (p refers to protein). gp91phox contains 1 flavin adenine dinucleotide (FAD) and 2 hemes as well as the NADPH binding site. p22phox has a C-terminal proline-rich sequence which serves as a binding site for cytosolic regulatory proteins. The two cytochrome subunits, gp91phox and p22phox appear to stabilize one another, since the genetic absence of either subunit, as in the inherited disorder chronic granulomatous disease (CGD), results in the absence of the partner subunit (Yu et al. (1997) *J. Biol. Chem.* 272, 27288-27294). Essential cytosolic proteins include p47phox, p67phox and the small GTPase Rac, of which there are two isoforms. p47phox and p67phox both contain $SH_3$ regions and proline-rich regions which participate in protein interactions governing assembly of the oxidase components during activation. The neutrophil enzyme is regulated in response to bacterial phagocytosis or chemotactic signals by phosphorylation of p47phox, and perhaps other components, as well as by guanine nucleotide exchange to activate the GTP-binding protein Rac.

ROI generated in many non-phagocytic tissues are now thought to originate from Nox enzymes. These Nox enzymes are homologs of gp91phox, the catalytic subunit of the phagocyte NADPH oxidase. The Nox family consists in human of seven unique gene products: Nox1, Nox2 (same as gp91phox), Nox3, Nox4, Nox5, Duox1 and Duox2. Each member of the Nox family has a specific expression pattern in tissues. For example, Nox1 is highly expressed in colonic epithelium, while Nox4 is highly expressed in kidney epithelium. Although these enzymes are thought to account for much of the ROI generated in many of these tissues, except for Nox2, the mechanism by which these enzymes are regulated is unknown. While not wishing to be bound to any particular theory, it is believed that the molecular candidates related to gp91phox and involved in ROI generation in cells have been located in the Nox and Duox family of proteins. (Lambeth et al. (2001) *Gene* May 16; 269 (1-2):131-40; Edens et al. (2001) *J. Cell Biol.* August 20: 154(4):879-91; Lambeth et al. (2000) *Trends Biochem Sci.* October 25, (10); 459-61)

However, regulatory proteins for this family of enzymes have not been determined. This deficiency has blocked the development of an in vitro system in which the enzymatic activity to generate ROIs can be analyzed. Furthermore, the regulatory proteins would provide an additional target for controlling ROI generation. Accordingly, what is needed is the identity of the regulators of proteins involved in ROI generation, particularly in non-phagocytic tissues and cells. What is also needed are the nucleotide sequences encoding for these proteins, and the primary sequences of the proteins themselves. Also needed are vectors designed to include nucleotides encoding for these proteins. Probes and PCR primers derived from the nucleotide sequence are needed to detect, localize and measure nucleotide sequences, including mRNA, involved in the synthesis of these proteins. In addition, what is needed is a means to transfect cells with these vectors. What is also needed are expression systems for production of these molecules. Also needed are antibodies directed against these molecules for a variety of uses including localization, detection, measurement and passive immunization.

SUMMARY OF THE INVENTION

The present invention solves the problems described above by providing novel nucleotide sequences and proteins. It is believed that these proteins may possess activity to affect ROI production either directly, or through modulation of the ability of the Nox family of enzymes to affect ROI production. In particular the present invention provides compositions comprising the nucleotide sequences SEQ ID NO:1, SEQ ID NO:3, SEQ ID NO:5, SEQ ID NO:7, and fragments thereof. SEQ ID NO:1 and fragments thereof code for the expression of the protein comprising SEQ ID NO:2 and fragments thereof, SEQ ID NO:3 and fragments thereof code for the expression of the protein comprising SEQ ID NO:4 and fragments thereof, SEQ ID NO:5 and fragments thereof code for the expression of the protein comprising SEQ ID NO: 6 and fragments thereof, and SEQ ID NO:7 and fragments thereof code for the expression of the protein comprising SEQ ID NO:8 and fragments thereof. In the present application, these proteins are called regulatory proteins.

While not wanting to be bound by the following statement, it is believed that these proteins may possess activity to affect ROI production and cellular proliferation either directly, or through modulation of the ability of the Nox family of enzymes to affect ROI production. Nox enzymes are NADPH dependent superoxide generating enzymes. They are part of a larger related family of proteins that generate ROI, including Nox proteins ("Nox" is an abbreviation for NADPH oxidase), and Duox proteins, ("Duox" is an abbreviation for dual oxidase). The present invention also provides vectors containing the nucleotide sequences for the Nox regulators, cells transfected with these vectors which produce the proteins comprising SEQ ID NO:2, SEQ ID NO:4, SEQ ID NO:6, SEQ ID NO:8 or fragments thereof, and antibodies to these proteins and fragments thereof. The present invention also provides methods for modulating cellular proliferation by administering vectors encoded for production of the proteins comprising SEQ ID NO:2, SEQ ID NO:4, SEQ ID NO: 6, or SEQ ID NO:8 and fragments thereof. The present invention further provides methods for stimulating cellular proliferation by administering the proteins comprising SEQ ID NO:2, SEQ ID NO:4, SEQ ID NO:6, or SEQ ID NO:8 and fragments thereof. The nucleotides sequences of the present invention are useful for the detection, localization and measurement of the nucleic acids encoding for the production of the proteins of the present invention. The antibodies of the present invention are useful for the detection, localization and measurement of the proteins of the present invention. These nucleotides and antibodies can be combined with other reagents in kits for the purposes of detection, localization and measurement.

Most particularly, the present invention involves a method for regulation of cell division or cell proliferation by modifying the activity or expression of the proteins described as SEQ ID NO:2, SEQ ID NO:4, SEQ ID NO: 6, or SEQ ID NO:8 or fragments thereof. These regulatory proteins, in their naturally occurring or expressed forms, are expected to be useful in drug development and the development of other therapies. For example candidate drugs may be developed by screening chemical and drug libraries to determine whether candidate drugs inhibit or stimulate ROI production or cellular proliferation induced by these regulatory proteins. Candidate drugs may be developed by screening chemical and drug libraries to determine whether candidate drugs affect the activity of these regulatory proteins to modulate the enzymatic activity of Nox enzymes. Such chemicals and drugs would likely be useful as treatments for cancer, prostatic hypertrophy, benign prostatic hypertrophy, hypertension, atherosclerosis and many other disorders involving abnormal cell growth or proliferation as described below. These regulatory proteins may be useful in any assays that relate to assessment of abnormal growth or cellular proliferation including cancer, prostatic hypertrophy, benign prostatic hypertrophy, hypertension, atherosclerosis, psoriasis, cardiovascular disease, proliferation of vessels, including but not limited to blood vessels and lymphatic vessels, arteriovenous malformation, vascular problems associated with the eye, and restenosis following angioplasty and many other disorders involving abnormal cell growth or proliferation. It is to be understood that modulation of activity with the proteins of the present invention may result in enhanced, diminished or absence of enzymatic activity. The drugs or other agents may directly affect the regulatory proteins of the present invention, interfere with the binding of the regulatory proteins of the present invention or interfere with the interaction between the regulatory proteins and the Nox enzymes which the regulatory proteins modulate. Modulation of the activity of these regulatory proteins may be useful in treatment of conditions associated with abnormal growth.

Drugs which affect the activity of the regulatory proteins represented in SEQ ID NO:2, SEQ ID NO:4, SEQ ID NO:6, SEQ ID NO:8 or fragments thereof, may also be combined with other therapeutics in the treatment of specific conditions. For example, these drugs may be combined with angiogenesis inhibitors in the treatment of cancer, with antihypertensives for the treatment of hypertension, and with cholesterol lowering drugs for the treatment of atherosclerosis.

Accordingly, an object of the present invention is to provide nucleotide sequences, or fragments thereof, encoding for the production of regulatory proteins, or fragments thereof, that are involved in the regulation of ROI production.

Another object of the present invention is to provide nucleotide sequences, or fragments thereof, encoding for the production of regulatory proteins, or fragments thereof, that are involved in the cellular proliferation or abnormal cell growth.

A further object of the present invention is to provide regulatory proteins (SEQ ID NO:2, SEQ ID NO:4, SEQ ID NO:6, SEQ ID NO:8) involved in the regulation of Nox enzymes such as Nox1, Nox3, Nox4 and Nox5.

Another object of the present invention is to provide vectors containing the nucleotide sequences, or fragments thereof encoding for the regulatory proteins.

Yet another object of the present invention is to provide cells transfected with these vectors.

Still another object of the present invention is to administer cells transfected with these vectors to animals and humans.

Another object of the present invention is to provide proteins, or fragments thereof, that are involved in regulating enzymes involved in ROI production.

Still another object of the present invention is to provide antibodies, including monoclonal and polyclonal antibodies, or fragments thereof, raised against proteins, or fragments thereof, that are involved in regulating enzymes involved in ROI production.

Another object of the present invention is to administer genes containing nucleotide sequences, or fragments thereof, encoding for the production of proteins, or fragments thereof, that are involved in regulating enzymes involved in ROI production, to animals and humans, and also to cells obtained from animals and humans.

Another object of the present invention is to administer antisense complimentary sequences of genes containing nucleotide sequences, or fragments thereof, encoding for the production of proteins, or fragments thereof, that are involved in regulating enzymes that are involved in ROI production, to animals and humans and also to cells obtained from animals and humans.

Yet another object of the present invention is to provide a method for stimulating or inhibiting cellular proliferation by administering vectors containing nucleotide sequences, or fragments thereof, encoding for the production of proteins, or fragments thereof, that are involved in regulating enzymes involved in ROI production, to animals and humans. It is also an object of the present invention to provide a method for stimulating or inhibiting cellular proliferation by administering vectors containing antisense complimentary sequences of nucleotide sequences, or fragments thereof, encoding for the production of proteins, or fragments thereof, that are involved in regulating enzymes that are involved in ROI production, to animals and humans. These methods of stimulating cellular proliferation are useful for a variety of purposes, including but not limited to, developing animal models of tumor formation, stimulating cellular proliferation of blood marrow cells following chemotherapy or radiation, or in cases of anemia.

Still another object of the present invention is to provide antibodies useful in immunotherapy against cancers expressing the proteins represented in SEQ ID NO:2, SEQ ID NO:4, SEQ ID NO:6, SEQ ID NO:8 or fragments thereof.

Yet another object of the present invention is to provide nucleotide probes useful for the detection, localization and measurement of proteins encoded by nucleotide sequences, or fragments thereof, encoding for the production of proteins, or fragments thereof, that are involved in regulating enzymes that are involved in ROI production.

Another object of the present invention is to provide antibodies useful for the detection, localization and measurement of nucleotide sequences, or fragments thereof, encoding for the production of proteins, or fragments thereof, that are involved in regulating enzymes that are involved in ROI production.

Another object of the present invention is to provide kits useful for detection of nucleotide sequences including the nucleotide sequences represented in SEQ ID NO:1, SEQ ID NO:3, SEQ ID NO:5, SEQ ID NO:7 or fragments thereof, that encode for proteins, or fragments thereof, that are involved in regulating enzymes that are involved in ROI production.

Still another object of the present invention is to provide kits useful for the localization of nucleotide sequences including the nucleotide sequences represented in SEQ ID NO:1, SEQ ID NO:3, SEQ ID NO:5, SEQ ID NO:7 or fragments thereof, that encode for proteins, or fragments thereof that are involved in regulating enzymes that are involved in ROI production.

Another object of the present invention is to provide kits useful for detection of proteins, including the proteins represented in SEQ ID NO:2, SEQ ID NO:4, SEQ ID NO:6, SEQ ID NO:8 or fragments thereof, that are involved in ROI production.

Yet another object of the present invention is to provide kits useful for detection and measurement of proteins, including the proteins represented in SEQ ID NO:2, SEQ ID NO:4, SEQ ID NO:6, SEQ ID NO:8 or fragments thereof, that are involved in regulating enzymes that are involved in ROI production.

Still another object of the present invention is to provide kits useful for localization of proteins, including the proteins represented in SEQ ID NO:2, SEQ ID NO:4, SEQ ID NO:6, SEQ ID NO:8 or fragments thereof, that are involved in regulating enzymes involved in ROI production.

Yet another object of the present invention is to provide kits useful for the detection, measurement or localization of nucleotide sequences, or fragments thereof, encoding for proteins, or fragments thereof, that are involved in regulating enzymes that are involved in ROI production, for use in diagnosis and prognosis of abnormal cellular proliferation related to ROI production.

Another object of the present invention is to provide kits useful for the detection, measurement or localization of proteins, or fragments thereof, that are involved in regulating enzymes that are involved in ROI production, for use in diagnosis and prognosis of abnormal cellular proliferation related to ROI production.

A further object of the present invention is to use the regulatory proteins represented in SEQ ID NO:2, SEQ ID NO:4, SEQ ID NO:6, SEQ ID NO:8 or fragments thereof, to screen for drugs that regulate the biological activity of these regulatory proteins.

Another object of the present invention is to use the regulatory proteins represented in SEQ ID NO:2, SEQ ID NO:4, SEQ ID NO:6, SEQ ID NO:8 or fragments thereof, to screen for drugs that regulate the cellular levels or activity of proteins in the Nox family These and other objects, features and advantages of the present invention will become apparent after a review of the following detailed description of the disclosed embodiments and the appended drawings.

DETAILED DESCRIPTION OF THE INVENTION

Figure 1:
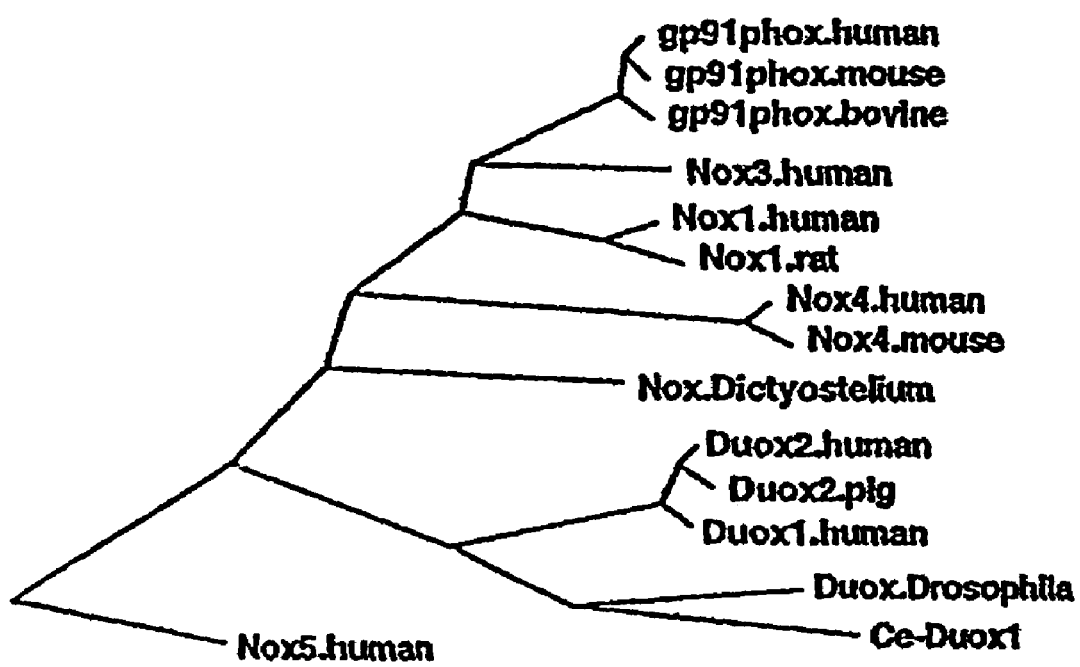
FIG. 1 is a dendrogram indicating the degree of similarity among the regulated family of proteins, and also includes the related plant enzymes.

The present invention provides nucleotide sequences encoding for the proteins p41Nox and its splice variants, and also provides the amino acid sequences for the proteins p41Nox and its splice variants. The p41Nox proteins of the present invention are also called regulatory proteins and Nox regulatory proteins in this application. The term "Nox" refers to "NADPH-oxidase." Nox proteins are part of a larger related family of proteins that generate ROI, including NOX proteins and Duox proteins, (Duox is an abbreviation for "dual oxidase"). As described herein, the term "p41nox" refers to the protein variants comprising amino acid sequences as set forth in SEQ ID NO:2, SEQ ID NO:4, SEQ ID NO:6, SEQ ID NO:8 or fragments or conservative substitutions thereof, and encoded, respectively, by the four DNA splice variants as set forth in SEQ ID NO:1, SEQ ID NO:3, SEQ ID NO:5, and SEQ ID NO:7 or fragments or conservative substitutions thereof. In particular, the present invention provides novel compositions comprising the nucleotide sequences SEQ ID NO:1, SEQ ID NO:3, SEQ ID NO:5, or SEQ ID NO:7, and fragments thereof.

It should be understood that some of the terminology used to describe the novel Nox regulatory proteins contained herein is different from the terminology in PCT/US99/26592, U.S. non-provisional application Ser. No. 09/437,568 and U.S. provisional application Ser. Nos. 60/251,364, 60/249,305, and 60/289,172. The terms mox and nox are equivalents.

The Nox proteins believed to be regulated by the p41Nox protein and its splice variant proteins described herein have homology to the gp91phox protein involved in ROI generation. The sequences for the Nox family have been previously disclosed in WO/0028031, WO/0187957, and WO/02081703, each of which is herein incorporated by reference in its entirety. While not wishing to be bound to any particular theory, it is believed that the p41Nox proteins regulate the activity of Nox proteins through allosteric interactions.

The p41Nox proteins described herein have a predicted molecular weight of approximately 41 kDa. They have a PX domain and 2 SH3 domains and show sequence homology (27% identity at the level of amino acids) with p47phox, a regulatory protein for gp91phox. As described in detail below, the p41Nox proteins of the present invention function in the regulation of cell growth, and are therefore implicated in diseases involving abnormal cell growth such as cancer. They may also function in innate immune mechanisms of epithelial tissue or other barrier cells, and hence may be involved in diseases of diminished ability to fight infections, or inflammatory conditions such as inflammatory bowel disease. The present invention describes p41Nox proteins found in humans, however, it is likely that the p41Nox genes/proteins are widely distributed among other multicellular organisms.

In addition to the nucleotide sequences described above, the present invention also provides vectors containing these nucleotide sequences and fragments thereof, cells transfected with these vectors which produce the proteins comprising SEQ ID NO:2, SEQ ID NO:4, SEQ ID NO:6, SEQ ID NO:8 and fragments thereof, and antibodies to these proteins and fragments thereof. The present invention also provides methods for stimulating cellular proliferation by administering vectors, or cells containing vectors, encoding for production of the proteins comprising SEQ ID NO:2, SEQ ID NO:4, SEQ ID NO:6, SEQ ID NO:8 and fragments thereof. The nucleotide sequences of the present invention are useful for the detection, localization and measurement of the nucleotide sequences encoding for the production of the proteins of the present invention. The antibodies of the present invention are useful for the detection, localization and measurement of the proteins of the present invention. These nucleotides and antibodies can be combined with other reagents in kits for the purposes of detection, localization and measurement. These kits are useful for diagnosis and prognosis of conditions involving cellular proliferation associated with production of reactive oxygen intermediates.

The present invention solves the problems described above by providing a composition comprising the nucleotide sequence SEQ ID NO:1 and fragments thereof. The present invention also provides a composition comprising the nucleotide sequence SEQ ID NO:3 and fragments thereof. The present invention additionally provides a composition comprising the nucleotide sequence SEQ ID NO: 5 and fragments thereof. The present invention further provides a composition comprising the nucleotide sequence of SEQ ID NO:7 and fragments thereof.

The present invention provides a composition comprising the protein SEQ ID NO:2 encoded by the nucleotide sequence SEQ ID NO:1. The present invention additionally provides a composition comprising the protein SEQ ID NO:4 encoded by the nucleotide sequence SEQ ID NO:3. The present invention further provides a composition comprising the protein SEQ ID NO:6 encoded by the nucleotide sequence SEQ ID NO:5. The present invention also provides a composition comprising the protein SEQ ID NO:8 encoded by the nucleotide sequence SEQ ID NO:7.

The present invention provides a composition comprising the protein SEQ ID NO:2 or fragments thereof, encoded by the nucleotide sequence SEQ ID NO:1 or fragments thereof. The present invention also provides a composition comprising the protein SEQ ID NO:4 or fragments thereof, encoded by the nucleotide sequence SEQ ID NO:3 or fragments thereof. The present invention additionally provides a composition comprising the protein SEQ ID NO:6 or fragments thereof, encoded by the nucleotide sequence SEQ ID NO:5 or fragments thereof. The present invention further provides a composition comprising the protein SEQ ID NO:8 or fragments thereof, encoded by nucleotide sequence SEQ ID NO:7 or fragments thereof.

The present invention also provides vectors containing the nucleotide sequences SEQ ID NO:1, SEQ ID NO:3, SEQ ID NO:5, or SEQ ID NO:7 and fragments thereof. The present invention also provides cells transfected with these vectors. In addition, the present invention provides cells stably transfected with the nucleotide sequence SEQ ID NO:1 or fragments thereof. The present invention also provides cells stably transfected with the nucleotide sequence SEQ ID NO:3 or fragments thereof. The present invention additionally provides cells stably transfected with the nucleotide sequence SEQ ID NO:5 or fragments thereof. The present invention further provides cells stably transfected with the nucleotide sequence SEQ ID NO:7 or fragments thereof.

The present invention provides cells stably transfected with the nucleotide sequence SEQ ID NO:1 or fragments thereof, which produce the protein SEQ ID NO:2 or fragments thereof. In addition, the present invention provides cells stably transfected with the nucleotide sequence SEQ ID NO:3 or fragments thereof which produce the protein SEQ ID NO:4 or fragments thereof. In addition, the present invention provides cells stably transfected with the nucleotide sequence SEQ ID NO:5 or fragments thereof which produce the protein SEQ ID NO:6 or fragments thereof. The present invention also provides cells stably transferred with the nucleotide sequence SEQ ID NO:7 or fragments thereof which produce the protein SEQ ID NO:8 or fragments thereof.

The present invention provides a method for modulating growth by administering cells stably transfected with the nucleotide sequence SEQ ID NO:1 or fragments thereof which produce the protein SEQ ID NO:2 or fragments thereof. The present invention also provides a method for modulating growth by administering cells stably transfected with the nucleotide sequence SEQ ID NO:3 or fragments thereof, which produce the protein SEQ ID NO:4 or fragments thereof. The present invention further provides a method of modulating growth by administering cells stably transfected with the nucleotide sequence SEQ ID NO:5 or fragments thereof, which produce the protein SEQ ID NO:6 or fragments thereof. The present invention also provides a method modulating growth by administering cells stably transfected with the nucleotide sequence SEQ ID NO:7 or fragments thereof, which produce the protein SEQ ID NO:8 or fragments thereof.

Specifically, the present invention provides a method for regulating Nox enzymes which in turn stimulate tumor formation by administering cells stably transfected with the nucleotide sequence SEQ ID NO:1 or fragments thereof, which produce the protein SEQ ID NO:2 or fragments thereof. The present invention also provides a method for modulating tumor formation by administering cells stably transfected with the nucleotide sequence SEQ ID NO:3 or fragments thereof, which produce the protein SEQ ID NO:4 or fragments thereof. The present invention further provides a method for modulating tumor formation by administering cells stably transfected with the nucleotide sequence SEQ ID NO:5 or fragments thereof, which produce the protein SEQ ID NO:6 or fragments thereof. The present invention also provides a method for modulating tumor formation by administrating cells stably transfected with the nucleotide sequence SEQ ID NO:7 or fragments thereof, which produce the protein SEQ ID NO:8 or fragments thereof.

The present invention may also be used to develop anti-sense nucleotide sequences to SEQ ID NO:1, SEQ ID NO:3, SEQ ID NO:5, SEQ ID NO:7 or fragments thereof. These anti-sense molecules may be used to interfere with translation of nucleotide sequences, such as SEQ ID NO:1, SEQ ID NO:3, SEQ ID NO:5, SEQ ID NO:7, or fragments thereof, that encode respectively, for proteins such as SEQ ID NO:2, SEQ ID NO:4, SEQ ID NO:6, SEQ ID NO:8 or fragments thereof. Administration of these anti-sense molecules, or vectors encoding for these anti-sense molecules, to humans and animals, would interfere with production of proteins such as SEQ ID NO:2, SEQ ID NO:4, SEQ ID NO:6, SEQ ID NO:8 or fragments thereof, thereby decreasing production of ROI and inhibiting cellular proliferation. These methods are useful in producing animal models for use in study of tumor development and vascular growth, and for study of the efficacy of treatments for affecting tumor and vascular growth in vivo.

The present invention also provides a method for high throughput screening of drugs and chemicals, which modulate the regulatory activity of the proteins of the present invention, thereby affecting cell division. Combinatorial chemical libraries may be screened for chemicals, which modulate the regulatory activity of these proteins. Drugs and chemicals may be evaluated based on their ability to modulate the regulatory activity of the expressed or endogenous proteins, including those represented by SEQ ID NO:2, SEQ ID NO:4, SEQ ID NO:6, SEQ ID NO:8 or fragments thereof. The drugs and chemicals may interfere with the transcription or translation or the regulatory proteins, act directly on the regulatory proteins, interfere with the interaction of the regulatory proteins and the Nox enzymes, or otherwise interfere with the biological activity of the regulatory proteins. Endogenous regulatory proteins may be obtained from many different tissues or cells, such as colon cells. Drugs may also be evaluated based on their ability to bind to the expressed or endogenous regulatory proteins represented by SEQ ID NO:2, SEQ ID NO:4, SEQ ID NO:6, SEQ ID NO:8 or fragments thereof. These regulatory proteins, in their naturally occurring or expressed forms, are expected to be useful in drug development and the development of other therapies. For example, candidate drugs may be developed by screening chemical and drug libraries to determine whether candidate drugs inhibit or stimulate ROI production or cellular proliferation induced by these regulatory proteins. Candidate drugs may be developed by screening chemical and drug libraries to determine whether candidate drugs affect the activity of these regulatory proteins to modulate the enzymatic activity of Nox enzymes. Such chemicals and drugs would likely be useful as treatments for cancer, prostatic hypertrophy, benign prostatic hypertrophy, hypertension, atherosclerosis and many other disorders involving abnormal cell growth or proliferation as described below. These regulatory proteins may be useful in any assays that relate to assessment of abnormal growth or cellular proliferation including cancer, prostatic hypertrophy, benign prostatic hypertrophy, hypertension, atherosclerosis, psoriasis, cardiovascular disease, proliferation of vessels, including but not limited to blood vessels and lymphatic vessels, arteriovenous malformation, vascular problems associated with the eye, and restenosis following angioplasty and many other disorders involving abnormal cell growth or proliferation. It is to be understood that modulation of activity with the proteins of the present invention may result in enhanced, diminished or absence of enzymatic activity. The drugs or other agents may directly effect the regulatory proteins of the present invention, interfere with the binding of the regulatory proteins of the present invention or interfere with the interaction between the regulatory proteins and the Nox enzymes which the regulatory proteins modulate. Modulation of the activity of these regulatory proteins may be useful in treatment of conditions associated with abnormal growth.

The activity of the p41Nox regulatory proteins shown in SEQ ID NO:2, SEQ ID NO:4, SEQ ID NO:6, and SEQ ID NO:8, or fragments thereof, regulate the reactions of Nox proteins which have NADPH-dependent reductase activity towards cytochrome c, nitrobluetetrazolium and other dyes. Expressed proteins or fragments thereof can be used for robotic screens of existing combinational chemical libraries. While not wanting to be bound by the following statement, it is believed that the NADPH or NADH binding site and the FAD binding site of the Nox proteins are useful for evaluating the ability of drugs and other compositions to bind to the Nox enzymes or to modulate their enzymatic activity. The p41Nox regulatory proteins are theorized to interact allosterically with the Nox proteins to modulate their activity. These regulatory proteins can be used alone or in combination in developing a high throughput drug screen.

The present invention also provides antibodies directed to the proteins SEQ ID NO:2, SEQ ID NO:4, SEQ ID NO:6, SEQ ID NO:8 and fragments thereof. The antibodies of the present invention are useful for a variety of purposes including localization, detection and measurement of the proteins SEQ ID NO:2, SEQ ID NO:4, SEQ ID NO:6, SEQ ID NO:8 and fragments thereof. The antibodies may be employed in kits to accomplish these purposes. These antibodies may also be linked to cytotoxic agents for selected killing of cells. The term antibody is meant to include any class of antibody such as IgG, IgM and other classes. The term antibody also includes a completely intact antibody and also fragments thereof, including but not limited to Fab fragments and Fab+Fc fragments.

The present invention also provides the nucleotide sequences SEQ ID NO:1, SEQ ID NO:3, SEQ ID NO:5, SEQ ID NO:7 and fragments thereof. These nucleotide sequences are useful for a variety of purposes including localization, detection, and measurement of messenger RNA involved in synthesis of the proteins represented as SEQ ID NO:2, SEQ ID NO:4, SEQ ID NO:6, SEQ ID NO:8 and fragments thereof and the localization, detection and measurement of messenger RNA involved in synthesis of the p41Nox proteins. These nucleotides may also be used in the construction of labeled probes for the localization, detection, and measurement of nucleic acids such as messenger RNA or alternatively for the isolation of larger nucleotide sequences containing the nucleotide sequences shown in SEQ ID NO:1, SEQ ID NO:3, SEQ ID NO:5, SEQ ID NO:7 or fragments thereof. These nucleotide sequences may be used to isolate homologous strands from other species using techniques known to one of ordinary skill in the art. These nucleotide sequences may also be used to make probes and complementary strands.

The term "mitogenic regulators" is used herein to mean any molecule that acts to affect cell division.

The term "animal" is used herein to mean humans and non-human animals of both sexes.

The terms "a", "an" and "the" as used herein are defined to mean one or more and include the plural unless the context is inappropriate.

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (b or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence can have at least 60%, at least 70%, at least 80%, at least 90%, or at least 95% identity with respect to the reference nucleotide sequence.

The phrase "moderately stringent hybridization" refers to conditions that permit a target-nucleic acid to bind a complementary nucleic acid. The hybridized nucleic acids will generally have at least about 60% identity, at least about 70% identity, more at least about 80% identity; at least about 90% identity; or at least about 95% identity. Moderately stringent conditions are conditions equivalent to hybridization in 50% formamide, 5× Denhart's solution, 5× saline sodium phosphate EDTA buffer (SSPE), 0.2% SDS (Aldrich) at about 42° C., followed by washing in 0.2×SSPE, 0.2% SDS (Aldrich), at about 42° C.

High stringency hybridization refers to conditions that permit hybridization of only those nucleic acid sequences that form stable hybrids in 0.018M NaCl at about 65° C., for example, if a hybrid is not stable in 0.018M NaCl at about 65° C., it will not be stable under high stringency conditions, as contemplated herein. High stringency conditions can be provided, for example, by hybridization in 50% formamide, 5× Denhart's solution, 5×SSPE, 0.2% SDS at about 42° C., followed by washing in 0.1×SSPE, and 0.1% SDS at about 65° C.

Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al. (Current Protocols in Molecular Biology (Supplement 47), John Wiley & Sons, New York (1999)).

Furthermore, one of skill in the art will recognize that, as mentioned above, individual substitutions, deletions or additions which alter, add or delete a single amino acid or a small percentage of amino acids (less than about 20%, typically less than about 10%, more typically less than about 5%, typically less than about 3%, typically less than about 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

When the peptides are relatively short in length (i.e., less than about 50 amino acids), they are often synthesized using standard chemical peptide synthesis techniques. Solid phase synthesis in which the C-terminal amino acid of the sequence is attached to an insoluble support followed by sequential addition of the remaining amino acids in the sequence is a preferred method for the chemical synthesis of the antigenic epitopes described herein. Techniques for solid phase synthesis are known to those skilled in the art.

Alternatively, the antigenic epitopes described herein are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

One of skill in the art will recognize that after chemical synthesis, biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

The genetic constructs of the present invention include coding sequences for different proteins, fragments thereof, and peptides. The genetic constructs also include epitopes or domains chosen to permit purification or detection of the expressed protein. Such epitopes or domains include DNA sequences encoding the glutathione binding domain from glutathione S-transferase, hexa-histidine, thioredoxin, hemagglutinin antigen, maltose binding protein, and others commonly known to one of skill in the art. The preferred genetic construct includes the nucleotide sequences of SEQ ID NO:1, SEQ ID NO:3, SEQ ID NO:5, SEQ ID NO:7 or fragments thereof. It is to be understood that additional or alternative nucleotide sequences may be included in the genetic constructs in order to encode for the following: a) multiple copies of the desired proteins, fragments thereof, or peptides; b) various combinations of the desired proteins, fragments thereof, or peptides; and c) conservative modifications of the desired proteins, fragments thereof, or peptides, and combinations thereof. Preferred proteins include the p41nox proteins shown as SEQ ID NO:2, SEQ ID NO:4, SEQ ID NO:6, SEQ ID NO:8 respectively, and fragments thereof or conservative substitutions thereof.

The nucleotide sequences of the present invention may also be employed to hybridize to nucleic acids such as DNA or RNA nucleotide sequences under high stringency conditions which permit detection, for example, of alternately spliced messages.

The genetic construct is expressed in an expression system such as in NIH 3T3 cells using recombinant sequences in a pcDNA-3 vector (Invitrogen, Carlsbad, Calif.) to produce a recombinant protein. Preferred expression systems include but are not limited to Cos-7 cells, insect cells using recombinant baculovirus, and yeast. It is to be understood that other expression systems known to one of skill in the art may be used for expression of the genetic constructs of the present invention. The preferred proteins of the present invention are the sequences referred to herein as p41nox or fragments thereof which have the amino acid sequences set forth in SEQ ID NO:2, SEQ ID NO:4, SEQ ID NO:6, and SEQ ID NO:8 respectively, or an amino acid sequence having amino acid substitutions as defined in the definitions that do not significantly alter the function of the recombinant protein in an adverse manner.

Construction of the Recombinant Gene

The desired gene is ligated into a transfer vector, such as pcDNA3, and the recombinants are used to transform host cells such as Cos-7 cells. It is to be understood that different transfer vectors, host cells, and transfection methods may be employed as commonly known to one of ordinary skill in the art. Four desired genes for use in transfection are shown in SEQ ID NO:1, SEQ ID NO:3, SEQ ID NO:5, and SEQ ID NO:7. For example, lipofectamine-mediated transfection and in vivo homologous recombination was used to introduce the SEQ ID NO:1 into NIH 3T3 cells.

The synthetic gene is cloned and the recombinant construct containing a Nox regulator gene is produced and grown in confluent monolayer cultures of a Cos-7 cell line. The expressed recombinant protein is then purified, preferably using affinity chromatography techniques, and its purity and specificity determined by known methods.

A variety of expression systems may be employed for expression of the recombinant protein. Such expression methods include, but are not limited to the following: bacterial expression systems, including those utilizing *E. coli* and *Bacillus subtilis*; virus systems; yeast expression systems; cultured insect and mammalian cells; and other expression systems known to one of ordinary skill in the art.

Transfection of Cells

It is to be understood that the vectors of the present invention may be transfected into any desired cell or cell line. Both in vivo and in vitro transfection of cells are contemplated as part of the present invention. Preferred cells for transfection include but are not limited to the following: fibroblasts (possibly to enhance wound healing and skin formation), granulocytes (possible benefit to increase function in a compromised immune system as seen in AIDS, and aplastic anemia), muscle cells, neuroblasts, stem cells, bone marrow cells, osteoblasts, B lymphocytes, and T lymphocytes.

Cells may be transfected with a variety of methods known to one of ordinary skill in the art and include but are not limited to the following: electroporation, gene gun, calcium phosphate, lipofectamine, and fugene, as well as adenoviral transfection systems.

Host cells transfected with the nucleotide sequences represented in SEQ ID NO:1, SEQ ID NO:3, SEQ ID NO:5, SEQ ID NO:7 or fragments thereof, are used to express the proteins SEQ ID NO:2, SEQ ID NO:4, SEQ ID NO:6, SEQ ID NO:8 respectively, or fragments thereof. Host cells transfected with the nucleotide sequences represented in SEQ ID NO:1, SEQ ID NO:3, SEQ ID NO:5, SEQ ID NO:7 or fragments thereof, are also used in screening assays for the development of drugs or other therapeutic compounds.

These expressed proteins, or fragments thereof, are used to raise antibodies. These antibodies may be used for a variety of applications, including but not limited to, immunotherapy against cancers expressing one of the Nox proteins, and for detection, localization and measurement of the proteins shown in SEQ ID NO:2, SEQ ID NO:4, SEQ ID NO:6, SEQ ID NO:8 or fragments thereof.

Purification and Characterization of the Expressed Proteins

The proteins of the present invention can be expressed as a fusion protein with a poly histidine component, such as a hexa histidine, and purified by binding to a metal affinity column using nickel or cobalt affinity matrices. The protein can also be expressed as a fusion protein with glutathione S-transferase and purified by affinity chromatography using a glutathione agarose matrix. The protein can also be purified by immunoaffinity chromatography by expressing it as a fusion protein, for example with hemagglutinin antigen. The expressed or naturally occurring protein can also be purified by conventional chromatographic and purification methods which include anion and cation exchange chromatography, gel exclusion chromatography, hydroxylapatite chromatography, dye binding chromatography, ammonium sulfate precipitation, precipitation in organic solvents or other techniques commonly known to one of skill in the art.

Methods of Assessing Activity of Expressed Proteins

Different methods are available for assessing the activity of the expressed regulatory proteins of the present invention, including but not limited to the proteins represented as SEQ ID NO:2, SEQ ID NO:4, SEQ ID NO:6, SEQ ID NO:8 conservative substitutions thereof, and fragments thereof. The following assays can be used to measure superoxide generation. Superoxide generation may be reflective of the any of the following conditions: modulatory action of the regulatory proteins on the Nox enzymes; the direct or indirect effects of the regulatory proteins on superoxide generation; the effect of drugs or other compounds, including potential therapeutic compounds, on the biological activity of the regulatory proteins, whether the compounds increase the activity of the regulatory proteins, decrease the activity of the regulatory proteins, affect the regulatory proteins directly or indirectly, interfere with the modulatory activity of the regulatory proteins on Nox enzymes, or otherwise modulate the effects of the regulatory proteins.

Assays of the Regulatory Proteins and Fragments Thereof for Superoxide Generation A. General Considerations.

The regulatory proteins, as well as the Nox enzymes that they regulate, may be expressed in COS-7 cells, NIH 3T3 cells, insect cells (using baculoviral technology) or other cells using methods known to one of skill in the art. Membrane fractions or purified protein are used for the assay. The assay may require or be augmented by other cellular proteins such as p47phox, p67phox, and Rac1, as well as potentially other unidentified factors (e.g., kinases or other regulatory proteins). Assays for superoxide generation may be performed using intact cells, for example, the p41Nox-transfected NIH 3T3 cells, or lysed cells. In principle, any of the assays listed below can be used to evaluate superoxide generation using intact cells. NBT reduction is a preferred assay method.

B. Cytochrome c Reduction.

NADPH or NADH is used as the reducing substrate, in a concentration of about 100 µM. Reduction of cytochrome c is monitored spectrophotometrically by the increase in absorbance at 550 nm, assuming an extinction coefficient of 21 mM$^{-1}$ cm$^{-1}$. The assay is performed in the absence and presence of about 10 µg superoxide dismutase. The superoxide-dependent reduction is defined as cytochrome c reduction in the absence of superoxide dismutase minus that in the presence of superoxide dismutase (Uhlinger et al. (1991) *J. Biol. Chem.* 266, 20990-20997). Acetylated cytochrome c may also be used, since the reduction of acetylated cytochrome c is thought to be exclusively via superoxide.

C. Nitroblue Tetrazolium Reduction.

For nitroblue tetrazolium (NBT) reduction, the same general protocol is used, except that NBT is used in place of cytochrome c. In general, about 1 mL of filtered 0.25% nitrotetrazolium blue (Sigma, St. Louis, Mo.) is added in Hanks buffer without or with about 600 Units of superoxide dismutase (Sigma) and samples are incubated at approximately 37° C. The oxidized NBT is clear, while the reduced NBT is blue and insoluble. The insoluble product is collected by centrifugation, and the pellet is re-suspended in about 1 mL of pyridine (Sigma) and heated for about 10 minutes at 100° C. to solubilize the reduced NBT. The concentration of reduced NBT is determined by measuring the absorbance at 510 µm, using an extinction coefficient of 11,000 M$^{-1}$ cm$^{-1}$. Untreated wells are used to determine cell number.

D. Luminescence.

Superoxide generation may also be monitored with a chemiluminescence detection system utilizing lucigenin (bis-N-methylacridinium nitrate, Sigma, St. Louis, Mo.). The sample is mixed with about 100 µM NADPH (Sigma, St. Louis, Mo.) and 10 µM lucigenin (Sigma, St. Louis, Mo.) in a volume of about 150 µL Hanks solution. Luminescence is monitored in a 96-well plate using a LumiCounter (Packard, Downers Grove, Ill.) for 0.5 second per reading at approximately 1 minute intervals for a total of about 5 minutes; the highest stable value in each data set is used for comparisons. As above, superoxide dismutase is added to some samples to prove that the luminescence arises from superoxide. A buffer blank is subtracted from each reading (Ushio-Fukai et al. (1996) *J. Biol. Chem.* 271, 23317-23321).

Nucleotides and Nucleic Acid Probes

The nucleotide sequences SEQ ID NO:1, SEQ ID NO:3, SEQ ID NO:5, SEQ ID NO:7 as well as fragments thereof and PCR primers thereof, may be used, respectively, for localization, detection and measurement of nucleic acids related to SEQ ID NO:1, SEQ ID NO:3, SEQ ID NO:5, SEQ ID NO:7 as well as fragments thereof. The nucleotide sequences SEQ ID NO:1, SEQ ID NO:3, SEQ ID NO:5, SEQ ID NO:7 are DNA splice variants of p41 nox and may be collectively referred to as p41nox in this application.

The nucleotide sequences SEQ ID NO:1, SEQ ID NO:3, SEQ ID NO:5, SEQ ID NO:7 as well as fragments and conservative substitutions thereof, may be used to create probes to isolate larger nucleotide sequences containing the nucleotide sequences SEQ ID NO:1, SEQ ID NO:3, SEQ ID NO:5, or SEQ ID NO:7 respectively. The nucleotide sequences SEQ ID NO:1, SEQ ID NO:3, SEQ ID NO:5, SEQ ID NO:7 as well as fragments thereof and conservative substitutions thereof, may also be used to create probes to identify and isolate p41Nox and Nox proteins in other species.

The nucleotide sequences described herein include messenger RNA coding for production of SEQ ID NO:2, SEQ ID NO:4, SEQ ID NO:6, SEQ ID NO:8 and fragments and conservative substitutions thereof. Such nucleotide sequences include but are not limited to cDNA probes. These probes may be labeled in a variety of ways known to one of ordinary skill in the art. Such methods include but are not limited to isotopic and non-isotopic labeling. These probes may be used for in situ hybridization for localization of nucleic acids such as mRNA encoding for SEQ ID NO:2, SEQ ID NO:4, SEQ ID NO:6, SEQ ID NO:8 and fragments and conservative substitutions thereof. Localization may be performed using in situ hybridization at both ultrastructural and light microscopic levels of resolution using techniques known to one of ordinary skill in the art.

These probes may also be employed to detect and quantitate nucleic acids and mRNA levels using techniques known to one of ordinary skill in the art including but not limited to solution hybridization.

Administration of the Nox Regulatory Proteins of the Present Invention

The proteins represented by SEQ ID NO:2, SEQ ID NO:4, SEQ ID NO:6, SEQ ID NO:8 or fragments or conservative substitutions thereof, are combined with a pharmaceutically acceptable carrier or vehicle to produce a pharmaceutical composition and are administered to animals. Such administration may occur for stimulation or modulation of growth or cellular proliferation directly or by modulating the activity of Nox enzymes. Administration may also occur for generation of antibodies.

The terms "pharmaceutically acceptable carrier or pharmaceutically acceptable vehicle" are used herein to mean any liquid including but not limited to water or saline, oil, gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The pharmaceutical compositions may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The pharmaceutical composition may be administered through different routes, such as oral, including buccal and sublingual, rectal, parenteral, aerosol, nasal, intramuscular, subcutaneous, intradermal, and topical. The pharmaceutical composition of the present invention may be administered in different forms, including but not limited to solutions, emulsions and suspensions, microspheres, particles, microparticles, nanoparticles, and liposomes.

The pharmaceutical composition may be stored at temperatures of from about 4° C. to −100° C. The pharmaceutical composition may also be stored in a lyophilized state at different temperatures including room temperature. The pharmaceutical composition may be sterilized through conventional means known to one of ordinary skill in the art. Such means include, but are not limited to filtration, radiation and heat. The pharmaceutical composition of the present invention may also be combined with bacteriostatic agents, such as thimerosal, to inhibit bacterial growth.

Administration may also occur for the production of polyclonal antibodies using methods known to one of ordinary skill in the art. The preferred animals for antibody production are rabbits and mice. Other animals may be employed for immunization with these proteins or fragments thereof. Such animals include, but are not limited to the following; sheep, horses, pigs, donkeys, cows, monkeys and rodents such as guinea pigs and rats. It is expected that from about 1 to 7 dosages may be required per immunization regimen. Initial injections may range from about 0.1 µg to 1 mg, with a preferred range of about 1 µg to 800 µg, and a more preferred range of from approximately 25 µg to 500 µg. Booster injections may range from 0.1 µg to 1 mg, with a preferred range of approximately 1 µg to 800 µg, and a more preferred range of about 10 µg to 500 µg.

The volume of administration will vary depending on the route of administration and the size of the recipient. For example, intramuscular injections may range from about 0.1 ml to 1.0 ml.

Adjuvants

A variety of adjuvants known to one of ordinary skill in the art may be administered in conjunction with the protein in the pharmaceutical composition for generation of antibodies. Such adjuvants include, but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; or combinations thereof.

Monoclonal antibodies can be produced using hybridoma technology in accordance with methods well known to those skilled in the art. The antibodies are useful as research or diagnostic reagents or can be used for passive immunization. The composition may optionally contain an adjuvant.

The polyclonal and monoclonal antibodies useful as research or diagnostic reagents may be employed for detection and measurement of SEQ ID NO:2, SEQ ID NO:4, SEQ ID NO:6, SEQ ID NO:8 and fragments or conservative substitutions thereof. Such antibodies may be used to detect these proteins in a biological sample, including but not limited to samples such as cells, cellular extracts, tissues, tissue extracts, biopsies, tumors, and biological fluids. Such detection capability is useful for detection of disease related to these proteins to facilitate diagnosis and prognosis and to suggest possible treatment alternatives.

Detection may be achieved through the use of immunocytochemistry, ELISA, radioimmunoassay or other assays as commonly known to one of ordinary skill in the art. The p41nox proteins, or fragments or conservative substitutions thereof, may be labeled through commonly known approaches, including but not limited to the following: radiolabeling, dyes, magnetic particles, biotin-avidin, fluorescent molecules, chemiluminescent molecules and systems, ferritin, colloidal gold, and other methods known to one of skill in the art of labeling proteins.

Administration of Antibodies

The antibodies directed to the proteins shown as SEQ ID NO:2, SEQ ID NO:4, SEQ ID NO:6, and SEQ ID NO:8 or directed to fragments or conservative substitutions thereof, may also be administered directly to humans and animals in a passive immunization paradigm. Antibodies directed to extracellular portions of SEQ ID NO:2, SEQ ID NO:4, SEQ ID NO:6, or SEQ ID NO:8 or fragments thereof bind to these extracellular epitopes. Attachment of labels to these antibodies facilitates localization and visualization of sites of binding. Attachment of molecules such as ricin or other cytotoxins to these antibodies helps to selectively damage or kill cells expressing SEQ ID NO:2, SEQ ID NO:4, SEQ ID NO:6, or SEQ ID NO:8 or fragments thereof.

Kits

The present invention includes kits useful with the antibodies, nucleic acid probes, labeled antibodies, labeled proteins or fragments thereof for detection, localization and measurement of SEQ ID NO:1, SEQ ID NO:2, SEQ ID NO:3, SEQ ID NO:4, SEQ ID NO:5, SEQ ID NO:6, SEQ ID NO:7, SEQ ID NO:8 or combinations thereof and fragments or conservative substitutions thereof. The diagnostic kits may also measure or detect the relative expression of the Nox regulatory proteins described herein.

Kits may be used for immunocytochemistry, in situ hybridization, solution hybridization, radioimmunoassay, ELISA, Western blots, quantitative PCR, and other assays for the detection, localization and measurement of these nucleic acids, proteins or fragments thereof using techniques known to one of skill in the art.

The nucleotide sequences shown in SEQ ID NO:1, SEQ ID NO:3, SEQ ID NO:5, SEQ ID NO:7 or fragments thereof, may also be used under high stringency conditions to detect alternately spliced messages related to SEQ ID NO:1, SEQ ID NO:3, SEQ ID NO:5, SEQ ID NO:7 or fragments thereof, respectively.

Fragments of SEQ ID NO:1, SEQ ID NO:3, SEQ ID NO:5, or SEQ ID NO:7 containing the relevant hybridizing sequence can be synthesized onto the surface of a chip array. RNA samples, e.g., from tumors, are then fluorescently tagged and hybridized onto the chip for detection. This approach may be used diagnostically to characterize tumor types and to tailor treatments and/or provide prognostic information. Such prognostic information may have predictive value concerning disease progression and life span, and may also affect choice of therapy.

The other present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Sequence Analysis and Cloning of p41Nox (SEQ ID NO: 1, SEQ ID NO:3, SEQ ID NO:5, and SEQ ID NO: 7) Encoding, Respectively, for Production of the p41Nox Proteins (SEQ ID NO:2, SEQ ID NO:4, SEQ ID NO:6, and SEQ ID NO:8)

Using the protein sequence of p47phox (GenBank Accession No. AAF34737) as a query sequence, the GenBank database was searched. Genomic sequence from chromosome 16 (GenBank Accession No. NT_010552) was identified that showed approximately 25-30% sequence identity at the predicted amino acid sequence level with p47phox. Based on this genomic sequence, Primer 1: 5'-AAACGTCAGACCGCGGCTGGTGGC-3' (SEQ ID NO:9); Primer 2: 5'-GTCCATCCCCTCATCGGGATCCTC-3' (SEQ ID NO:10); and Primer 3: 5'-TCAGGAATCTGCAGCCTGGAAGCC-3' (SEQ ID NO:11) were designed.

SEQ ID NO:9 and SEQ ID NO:10 were used in RT-PCR experiments to look for expression in a series of normal and cancer cell lines. A ~350 bp PCR product was seen in RNA from human fetal kidney, liver, lung and T84 colon cancer cells. RNA from T84 cells and human fetal liver was then used to amplify the full-length p41Nox by PCR using SEQ ID NO:10 and SEQ ID NO:11. The PCR fragments obtained were about 1.1 kb in size, and were subcloned by TA cloning into the pCR2.1 vector. Thirteen unique clones were positive for the p41Nox sequence based on PCR using SEQ ID NO:10 and SEQ ID NO:11. These were sequenced, and contained the sequence for the four p41Nox variants, SEQ ID NO:1, SEQ ID NO:3, SEQ ID NO:5, and SEQ ID NO:7.

Secretion signal sequences were predicted according to web-based SMART program (version 3.1) at EMBL (http://www.smart.embl-heidelberg.de/smart/). Prediction of open reading frames (ORF) was carried out using the EditSeq program (DNASTAR), and phylogenetic analyses and multiple sequence alignment were carried out using the clustal method using the Megalign program (DNASTAR). Transmembrane alpha helices were predicted using the TMHMM algorithms through the Center for Biological Sequence Analysis (http://genome.cbs.dtu.dk/services/TMHMM/).

Total RNA was extracted from cell lines with Trizol (Life Technologies, Gaithersburg, Md.) based on the manufacturer's protocol or according to (Ishii et al., 1999) for glioma cell lines. RNAs were reverse transcribed into first-strand cDNA with Superscript II (Life Technologies, Gaithersburg, Md.) using oligo-dT according on the method provided by the manufacturer.

EXAMPLE 2

Real Time RT-PCR of p41Nox (SEQ ID NO: 1, SEQ ID NO:3, SEQ ID NO:5, and SEQ ID NO: 7).

G3PDH was used as a control. The G3PDH PCR product was purified using a QIAquick PCR purification kit (QIAGEN, Valencia, Calif.) and quantified using absorbance at 260 nm using a BECKMAN DU640B spectrophotometer. The standard curve for G3PDH was constructed using 10-fold serial dilutions of a known concentration of G3PDH PCR product in distilled water. Real time PCR amplification was carried out using a LightCycler (Roche Molecular Biochemicals, Indianapolis, Ind.) in a PCR reaction containing 0.2 µM of each primer, 1:84,000 SYBR Green I (Molecular Probes, Eugene, Oreg.) and Advantage 2 Polymerase Mix (Clontech, Palo Alto, Calif.). Amplification was carried out for 36 cycles of denaturation (95° C., 0 s, ramp rate 20° C./s), annealing (65° C., 5 s, ramp rate 20° C./s) and extension (72° C., 30 s ramp rate 20° C./s). Fluorescence was monitored at the end of each extension phase. Quantitation and melting curve were analyzed with the LightCycler software. RT-PCR confirmed expression in the colon. The ratio of copies of unknown to standard G3PDH was then calculated.

EXAMPLE 3

Northern Blotting of p41Nox (SEQ ID NO: 1, SEQ ID NO:3, SEQ ID NO:5, and SEQ ID NO: 7)

The Human Fetal and Adult Multiple Tissue Northern Blot (Clontech, Palo Alto, Calif.) was hybridized with $^{32}$P-random primer-labeled p41Nox probe according to the manufacturer's instructions. The probes were prepared by PCR with primers for p41Nox encoding nucleotide sequences SEQ ID NO:1, SEQ ID NO:3, SEQ ID NO:5, or SEQ ID NO:7. The PCR products represent coding sequences.

EXAMPLE 4

Transfection of NIH 3T3 Cells with SEQ ID NO:1, SEQ ID NO:3, SEQ ID NO:5, or SEQ ID NO: 7.

The nucleotide sequences SEQ ID NO:1, SEQ ID NO:3, SEQ ID NO:5, and SEQ ID NO:7, encoding for production of the p41Nox proteins (SEQ ID NO:2, SEQ ID NO:4, SEQ ID NO:6, and SEQ ID NO:8), respectively, are separately subcloned into the Not1 site of the pEF-PAC vector (obtained from Mary Dinauer, Indiana University Medical School, Indianapolis, Ind.) which has a puromycin resistance gene. Transfection is carried out as described in Sambrook et al., Molecular Cloning, A Laboratory Manual, Volumes 1-3, 2nd edition, Cold Spring Harbor Laboratory Press, N.Y., 1989. The SEQ ID NO:1, SEQ ID NO:3, SEQ ID NO:5, and SEQ ID NO:7 in pEF-PAC and the empty vector are separately transfected into NIH 3T3 cells using Fugene 6 (Boeringer Mannheim).

$10^5$ to $10^3$ cells stably transfected separately with p41Nox gene SEQ ID NO:1, SEQ ID NO:3, SEQ ID NO:5, or SEQ ID NO:7 or with empty vector are prepared in 0.3% warm (40° C.) agar solution containing DMEM and 10% calf serum. Cells are distributed onto a hardened 0.6% agar plate prepared with DMEM and 10% calf serum. After three weeks in culture (37° C., 5% $CO_2$) colony formation is observed by microscopy.

About $2 \times 10^6$ cells maintained in DMEM containing 10% calf serum are transfected with 10 μg of DNA. After 2 days, cells are split and selected in the same medium containing 1 mg/ml puromycin. Colonies that survive in selection media for 10 to 14 days are subcultured continuously in the presence of puromycin.

Cells which are stably transfected with the empty vector and cultured in soft agar for 3 weeks as above do not display anchorage independent growth. In contrast, NIH 3T3 cells which are stably transfected with the polynucleotides (SEQ ID NO:1, SEQ ID NO:3, SEQ ID NO:5, or SEQ ID NO:7) encoding, respectively, for p41Nox proteins (SEQ ID NO:2, SEQ ID NO:4, SEQ ID NO:6, or SEQ ID NO:8) cultured for 3 weeks in soft agar demonstrate anchorage independent growth of colonies. Transfected cells exhibit a transformed-like morphology, similar to that seen with (V12) Ras-transfected cells, characterized by long spindle-like cells.

EXAMPLE 5

Expression of p41Nox (SEQ ID NO:1, SEQ ID NO:3, SEQ ID NO:5, or SEQ ID NO: 7) in Transfected NIH 3T3 Cells To verify the expression of p41Nox mRNA after transfection, RT-PCR and Northern blotting are performed. Total RNAs are prepared from $10^6$ cells using the High Pure RNA Isolation Kit (Boeringer Mannheim) or Rneasy kit (Qiagen). cDNAs for each colony are prepared from 1-2 μg of total RNA using Advantage RT-PCR Kit (ClonTech). PCR amplification is performed using primers, SEQ ID NO: 9. For Northern blotting, 10-20 μg of total RNA is separated on a 1% agarose formaldehyde gel and transferred to a nylon filter. After ultraviolet (UV) cross-linking, filters are used for Northern blotting assay as described in Example 3. Colonies expressing large amounts of p41Nox are chosen for further analysis.

EXAMPLE 6

NADPH-Dependent Superoxide Generation Assay

In one embodiment of the present invention, NIH 3T3 cells stably transfected with the human p4 Nox gene (SEQ ID NO:1, SEQ ID NO:3, SEQ ID NO:5, or SEQ ID NO:7) and optionally the Nox enzymes previously disclosed in WO/0028031, WO/0187957, and WO/02081703, are analyzed for superoxide generation using the lucigenin (Bis-N-methylacridinium luminescence assay (Sigma, St. Louis, Mo., Li et al. (1998) *J. Biol. Chem.* 273, 2015-2023). Cells are washed with cold Hank's solution and homogenized on ice in Hank's buffer containing 15% sucrose using a Dounce homogenizer. Cell lysates are frozen immediately in a dry ice/ethanol bath. For the assay, 30 μg of cell lysate is mixed with 200 μM NADPH and 500 μM lucigenin. Luminescence is monitored using a LumiCounter (Packard) at three successive one minute intervals and the highest value was used for comparison. Protein concentration is determined by the Bradford method.

Superoxide generation is monitored in lysates from some of the stably transfected cell lines and is compared with superoxide generation by the untransfected NIH 3T3 cell lysates. The luminescent signal is inhibited by superoxide dismutase and the general flavoprotein inhibitor diphenylene iodonium, but is unaffected by added recombinant human p47phox, p67phox and Rac1(GTP-γS), which are essential cytosolic factors for the phagocyte respiratory-burst oxidase.

In an alternate and preferred embodiment of the present invention, cells that are stably transfected with p41Nox (SEQ ID NO:1, SEQ ID NO:3, SEQ ID NO:5, or SEQ ID NO:7) or with empty vector (NEF2) are grown in 10 cm tissue culture plates in medium containing DMEM, 10% calf serum, 100 units/ml penicillin, 100 μg/ml streptomycin, and 1 μg/ml puromycin to approximately 80% confluency. Cells (five tissue culture plates of each cell type) are washed briefly with 5 ml phosphate buffered saline (PBS) then dissociated from the plates with PBS containing 5 mM EDTA. Cells are pelleted by centrifuging briefly at 1000×g.

To permeabilize the cells, freeze thaw lysis is carried out and this is followed by passage of the cell material through a small bore needle. The supernatant is removed and the cells are frozen on dry ice for 15 minutes. After cells are thawed, 200 μl lysis buffer (Hank's Buffered Salt Solution—HBBS) containing a mixture of protease inhibitors from Sigma (Catalog no. P2714) is added. Cells on ice are passed through an 18 gauge needle 10 times and 200 μl of HBSS buffer containing 34% sucrose was added to yield a final concentration of 17% sucrose. Sucrose appeared to enhance stability upon storage. The combination of freeze-thawing and passage through a needle results in lysis of essentially all of the cells, and this material is referred to as the cell lysate.

The cell lysates are assayed for protein concentration using the BioRad protein assay system. Cell lysates are assayed for NADPH-dependent chemiluminescence by combining HBSS buffer, arachidonic acid, and 0.01-1 μg protein in assay plates (96 well plastic plates). The reaction is initiated by adding 1.5 mM NADPH and 75 μM lucigenin to the assay mix to give a final concentration of 200 μM NADPH and 10 μM lucigenin, and the chemiluminescence is monitored immediately. The final assay volume is 150 μl. The optimal arachidonic acid concentration is between 50-100 μM. A Packard Lumicount luminometer is used to measure chemiluminescence of the reaction between lucigenin and superoxide at 37° C. The plate is monitored continuously for 60 minutes and the maximal relative luminescence unit (RLU) value for each sample is used for the graph.

The presence of NaCl or KCl within a concentration range of 50-150 μM is important for optimal activity. $MgCl_2$ (1-5 mM) further enhanced activity by about 2-fold. This cell-free assay is useful for screening modulators (inhibitors or stimulators) of the Nox enzymes. The modulators may act directly or indirectly on the p41 regulatory proteins, inhibit or stimulate the biological activity of the regulatory proteins or interfere with the modulation of Nox enzymes by the regulatory proteins. The assay may also be used to detect Nox NADPH-oxidase activity in general and to screen for modulators (inhibitors or stimulators) of the Nox family of enzymes.

EXAMPLE 7

Nitro Blue Tetrazolium Reduction by Superoxide Generated by NIH 3T3 Cells Transfected with the p41Nox (SEQ ID NO:1, SEQ ID NO:3, SEQ ID NO:5, or SEQ ID NO: 7)

Superoxide generation by intact cells is monitored by using superoxide dismutase-sensitive reduction of nitroblue tetrazolium. NEF2 (vector alone control), and p41Nox (SEQ ID NO:1, SEQ ID NO:3, SEQ ID NO:5, or SEQ ID NO:7-transfected), cells are plated in six well plates at 500,000 cells per well. About 24 hours later, medium is removed from cells and the cells are washed once with 1 mL Hanks solution (Sigma, St. Louis, Mo.). About 1 mL of filtered 0.25% Nitro blue tetrazolium (NBT, Sigma) is added in Hanks without or with 600 units of superoxide dismutase (Sigma) and cells are incubated at 37° C. in the presence of 5% $CO_2$. After 8 minutes the cells are scraped and pelleted at more than 10,000 g. The pellet is re-suspended in 1 mL of pyridine (Sigma) and heated for 10 minutes at 100° C. to solubilize the reduced NBT. The concentration of reduced NBT is determined by measuring the absorbance at 510 nm, using an extinction coefficient of 11,000 $M^{-1}$ $cm^{-1}$. Some wells are untreated and used to determine cell number. Because superoxide dismutase is not likely to penetrate cells, superoxide must be generated extracellularly. The amount of superoxide generated by these cells is about 5-10% of that generated by activated human neutrophils.

EXAMPLE 8

Expression of Human p41Nox Protein (SEQ ID NO:2, SEQ ID NO:4, SEQ ID NO:6 or SEQ ID NO:8) in a Baculovirus Expression System SEQ ID NO:2, SEQ ID NO:4, SEQ ID NO:6 or SEQ ID NO:8 is also expressed in insect cells using recombinant baculovirus. To establish the p41Nox expressing virus systems, the p41Nox gene (SEQ ID NO:1, SEQ ID NO:3, SEQ ID NO:5, or SEQ ID NO:7) is initially cloned separately into the pBacPAK8 vector (Clontech, Palo Alto, Calif.) and recombinant baculovirus is constructed using standard methods according to manufacturer's protocols. Briefly, PCR amplified p41Nox DNA is cloned into the KpnI and EcoRI site of the vector. Primers used for PCR amplification are SEQ ID NO: 10 and SEQ ID NO:11. Sf9 insect cells ($2 \times 10^6$ cells) are infected with 0.5 mg of linearized baculovirus DNA sold under the trademark BACULOGOLD® (PharMingen, San Diego, Calif.) and 5 mg pBacPAC8 p41Nox using Transfection Buffers A and B (PharMingen, San Diego, Calif.). After 5 days, the supernatants containing recombinant viruses are harvested and amplified by infecting fresh sf9 cells for 7 days. Amplification is carried out three times and the presence of the recombinant viruses containing p41Nox DNA is confirmed by PCR using the same primers. After three times amplification of viruses, plaque purification are carried out to obtain the high titer viruses. Approximately $2 \times 10^8$ sf9 cells in agar plates are infected for 5 days with serial dilutions of virus and are dyed with neutral red for easy detection of virus plaques. Selected virus plaques are extracted and the presence of the human p41Nox DNA is confirmed again by PCR.

EXAMPLE 9

Antibodies to p41Nox Regulatory Proteins (SEQ ID NO:2, SEQ ID NO:4, SEQ ID NO:6, and SEQ ID NO:8)

Polyclonal antibodies are raised separately in rabbits against p41Nox splice variants (SEQ ID NO:2, SEQ ID NO:4, SEQ ID NO:6, or SEQ ID NO:8). Proteins are separately conjugated to keyhole limpet hemocyanin (KLH) using glutaraldehyde.

Antigens are injected into different rabbits initially in complete Freund's adjuvant, and are boosted 4 times with antigen in incomplete Freund's adjuvant at intervals of every three weeks. Approximately 0.1 mg to 1 mg of peptide is administered at each injection. Blood is drawn 1 week after each boost and a terminal bleed is carried out 2 weeks after the final boost. Anti p41Nox antibodies are purified on affinity columns to which are bound p41Nox (SEQ ID NO:2, SEQ ID NO:4, SEQ ID NO:6, or SEQ ID NO:8) using techniques known to one of ordinary skill in the art. Unbound protein is washed away with 20 ml of buffer. Elution of the antibodies from the gel was performed with 6 ml of elution buffer (100 mM glycine/HCl, pH 2.5, 200 mM NaCl, and 0.5% Triton X-100). The eluate is then neutralized by adding 0.9 ml of 1 M Tris/HCl, pH 8.0.

The detection of antigens is performed using an enhanced chemiluminescence kit (Amersham, Buckinghamshire, UK). The affinity purified antibodies to p41Nox are used at a dilution of 1:1000 in a Western blot in which a total of 10 μg of protein is added to each lane.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. An isolated nucleotide sequence encoding a protein comprising the amino acid sequence set forth as SEQ ID NO:4, a deletion thereof, an addition thereto, or a substitution thereto of less than 5% of the amino acid sequence, wherein the protein regulates an enzyme involved in the production of reactive oxygen intermediates.

2. The nucleotide sequence of claim 1, wherein the nucleotide sequence comprises the nucleotide sequence set forth as SEQ ID NO:1, SEQ ID NO:3, SEQ ID NO:5, or SEQ ID NO:7.

3. A vector, wherein the vector comprises the isolated nucleotide sequence of claim 1.

4. The vector of claim 3, wherein the nucleotide sequence to comprises SEQ ID NO:1, SEQ ID NO:3, SEQ ID NO:5, or SEQ ID NO:7.

5. An isolated cell comprising the vector of claim 3.

6. An isolated cell comprising the vector of claim 4.

7. A method of determining an effect of a compound on superoxide production comprising:
measuring a first level of superoxide production in the isolated host cell of claim 5,
contacting the host cell with the compound and measuring a second level of superoxide production; and,
comparing the first level and the second level of superoxide production by the host cell, thereby determining the effect of the compound on superoxide production.

8. The isolated nucleic acid sequence of claim 1, encoding a protein comprising an amino acid sequence set forth as SEQ ID NO: 4 or a conservative substitution of less than 1% of the amino acid sequence set forth as SEQ ID NO: 4.

9. The isolated nucleic acid sequence of claim 1, wherein the nucleic acid sequence encodes a protein comprising an amino acid sequence set forth as SEQ ID NO: 4.

10. The isolated nucleic acid sequence of claim 1, wherein the nucleic acid sequence encodes a protein comprising an amino acid sequence set forth as SEQ ID NO: 6.

11. The isolated nucleic acid sequence of claim 1, wherein the nucleic acid sequence encodes a protein comprising an amino acid sequence set forth as SEQ ID NO: 8.

12. The isolated nucleic acid sequence of claim 1, wherein the nucleic acid sequence encodes a protein comprising an amino acid sequence set forth as SEQ ID NO: 8.

13. The isolated nucleic acid sequence of claim 1, wherein the nucleic acid sequence comprises SEQ ID NO: 3.

14. The isolated nucleic acid sequence of claim 1, wherein the nucleic acid sequence comprises SEQ ID NO: 1.

15. The isolated nucleic acid sequence of claim 1, wherein the nucleic acid sequence comprises SEQ ID NO: 5.

16. The isolated nucleic acid sequence of claim 1, wherein the nucleic acid sequence comprises SEQ ID NO: 7.

17. A vector comprising the nucleotide sequence of claim 8.

18. An isolated host cell comprising the nucleotide sequence of claim 14.

19. A method of determining an effect of a compound on superoxide production comprising:
measuring a first level of superoxide production in the isolated host cell of claim 18;
contacting the host cell with the compound and measuring a second level of superoxide production; and
comparing the first level and the second level of superoxide production by the host cell, thereby determining the effect of the compound of superoxide production.

20. A method of determining an effect of a compound on superoxide production comprising:
measuring a first level of superoxide production in the isolated host cell of claim 6;
contacting the host cell with the compound and measuring a second level of superoxide production; and
comparing the first level and the second level of superoxide production by the host cell, thereby determining the effect of the compound on superoxide production.

* * * * *